United States Patent [19]
Nakai et al.

[11] Patent Number: 5,691,341
[45] Date of Patent: *Nov. 25, 1997

[54] APOPTOSIS REGULATING COMPOSITION

[75] Inventors: Satoru Nakai; Koutoku Aihara, both of Tokushima-ken; Hideo Tanaka, Tokushima; Hitomi Iba, Wakayama; Kazuyoshi Kawai, Tokushima-ken; Hiroyuki Ichikawa, Tokushima; Seiji Akamatsu, Naruto; Fumio Saito, Takasaki; Michiaki Tominaga, Tokushima-ken; Masakazu Adachi, Takasaki, all of Japan

[73] Assignee: Otsuka Pharmaceutical Co., Ltd., Tokyo, Japan

[*] Notice: The term of this patent shall not extend beyond the expiration date of Pat. No. 5,464,833.

[21] Appl. No.: 520,478

[22] Filed: Aug. 29, 1995

Related U.S. Application Data

[62] Division of Ser. No. 211,818, filed as PCT/JP93/01144 Aug. 12, 1993, Pat. No. 5,464,833.

[30] Foreign Application Priority Data

Aug. 19, 1992 [JP] Japan ................................ 5-220373

[51] Int. Cl.$^6$ .................. A61K 31/495; A61K 31/50; A61K 31/525
[52] U.S. Cl. ................ 514/254; 514/249; 514/250; 514/251; 514/255
[58] Field of Search .................. 514/249, 250, 514/251, 255, 254

[56] References Cited

FOREIGN PATENT DOCUMENTS

| A1 0552373 | 7/1993 | European Pat. Off. . |
| 6-012248 | of 1994 | Japan . |
| WO 9311769 | 6/1993 | WIPO . |

OTHER PUBLICATIONS

Carter et al, Chemotherapy of Cancer, 2nd Ed. John Wiley & Sons, N.Y, N.Y, pp. 362–365 (1981).

S. Nakai et al., *Differentiation–inducing activity of 3,4–dihydro–6–[4–(3,4–dimethoxybenzoy)–1–piperazinyl]–2(1H)quinolinone (vesnarinone) against tumor leukemia and solid tumor cells, Biomed. Pharmacother*, vol. 46, Sep. 1992, p. 308, abstract No. 139. Abstract only.

Bush et al, *Effects of OPC–8212, a New Positive Inotropic Agent on the Haemopoictic system in Vitro*, Exp. Hematol., vol. 19, Jul. 1991, p. 490, abstract No. 125. Abstract only.

Feldman et al., *Usefulness of OPC–8212, a Quinolinone Derivative, for Chronic Congestive Heart Failure in Patients with Ischemic Heart Disease or Idiopathic Dilated Cardiomyopathy*, AM. J. Cariol., vol. 68, Nov. 1991, pp. 1203–1210.

Levine et al., *Elevated Circulating Levels of Tumor Necrosis Factor in Severe Chronic Heart Failure*, The New England Journal of Medicine, vol. 323, Jul. 1990, pp. 236–241.

Rathbun et al., *Current and investigational therapies for AIDS–associated Mycobacterium avium complex disease*, Clin. Pharmacy, Ther. Rev., vol. 10, Apr. 1991, pp. 280–291.

*Primary Examiner*—Jerome D. Goldberg
*Attorney, Agent, or Firm*—Sughrue, Mion, Zinn, Macpeak & Seas, PLLC

[57] ABSTRACT

Apoptosis regulating compositions each comprising a member selected from a series of carbostyril derivatives and salts thereof, inclusive of carbostyril derivatives of general formula (1)

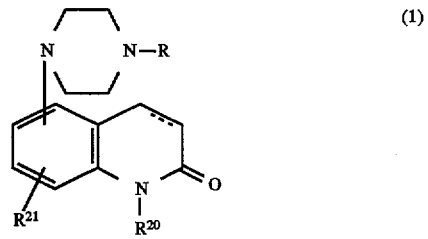

and salts thereof, as an active ingredient are provided.

The apoptosis regulating compositions of the invention are of use as anticancer agents, antiretrovirus agents, therapeutic agents for autoimmune diseases, therapeutic agents for thrombocytopenia, therapeutic agents for Alzheimer's disease, therapeutic agents for diseases of the liver, and cancer metastasis inhibitors, among others.

16 Claims, No Drawings

APOPTOSIS REGULATING COMPOSITION

This is a Divisional of application Ser. No. 08/211,818, filed Apr. 19, 1994, now U.S. Pat. No. 5,464,833.

The present invention relates to a novel apoptosis regulating composition.

The apoptosis regulating composition of the invention comprises, as an active ingredient, at least one member of the class consisting of carbostyril derivatives represented by any of the following general formula (1) through general formula (6) (hereinafter referred to as compound (1) through compound (6) respectively) and 6-[4-(3,4-dimethoxybenzoyl)-1-1,2,3,4-tetrahydropyrazyl]-3,4-dihydrocarbostyril (hereinafter referred to as compound (7)) inclusive of salts thereof.

(1) Carbostyril derivatives of the following general formula

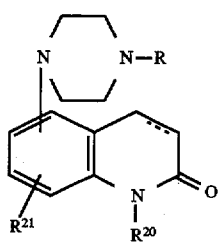

(1)

wherein R is a benzoyl group which may optionally have, on the phenyl ring thereof, one to three substituents each selected from the group consisting of lower alkoxy groups, halogen atoms, lower alkyl groups, lower alkanoylamino groups and lower alkylthio groups; a lower alkylenedioxybenzoyl group; a hydrogen atom; a pyridylcarbonyl group; a lower alkanesulfonyl group; a lower alkynyl group; or a phenyl-lower alkyl group which may optionally have, on the phenyl ring thereof, one to three substituents each selected from the group consisting of lower alkoxy groups, halogen atoms and lower alkyl groups; the carbon-carbon bond between the 3 and 4 positions of the carbostyril skeleton is a single bond or a double bond; $R^{20}$ is a hydrogen atom, a lower alkyl group, a lower alkenyl group, a lower alkynyl group or a phenyl-lower alkyl group; and $R^{21}$ is a hydrogen atom or a lower alkoxy group; provided, however, that where both of $R^{20}$ and $R^{21}$ are hydrogen atoms, R should not be a benzoyl group which may have a lower alkoxy group as a phenyl ring substituent; and salts thereof;

(2) Carbostyril derivatives of the following general formula

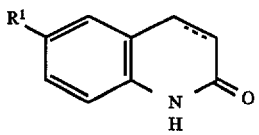

(2)

wherein $R^1$ is a group of the formula

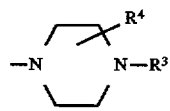

($R^3$ being a hydrogen atom or a benzoyl group and $R^4$ being an oxo group) and the carbon-carbon bond between the 3 and 4 positions of the carbostyril skeleton is a single bond or a double bond; and salts thereof;

(3) Carbostyril derivatives of the following general formula

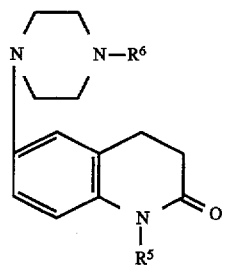

(3)

wherein $R^5$ is a lower alkanoyl group, a lower alkoxycarbonyl group, a lower alkoxycarbonyl-lower alkyl group, a phenyl-lower alkyl group having a lower alkanoyloxy group or a hydroxyl group on the phenyl ring thereof, or a benzoyl group which may optionally have, on the phenyl ring thereof, at least one substituent selected from the group consisting of a hydroxy group and amino groups optionally having a lower alkyl group, or a naphthoyl group, and $R^6$ is a benzoyl group which may optionally have at least one lower alkoxy group on the phenyl ring thereof; and salts thereof;

(4) Carbostyril derivatives of the following general formula

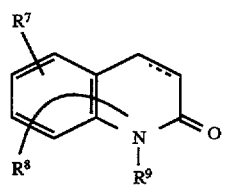

(4)

wherein $R^7$ is a piperazinyl group, $R^8$ is a hydrogen atom or a lower alkyl group, $R^9$ is a hydrogen atom or a phenyl-lower alkyl group, and the carbon-carbon bond between the 3 and 4 positions of the carbostyril skeleton is a single bond or a double bond; and salts thereof;

(5) Carbostyril derivatives of the following general formula

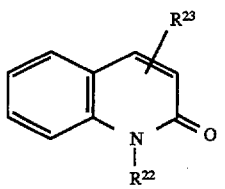

(5)

wherein $R^{22}$ is a $C_1$-$C_{16}$ alkyl group, a phenyl-lower alkoxycarbonyl-lower alkyl group, an amido-lower alkyl group which may optionally have at least one lower alkyl group, or a phenyl-lower alkyl group and $R^{23}$ is a piperazinyl group which may optionally have a lower alkyl group in the 4 position of the piperazine ring; and salts thereof;

(6) Carbostyril derivatives of the following general formula

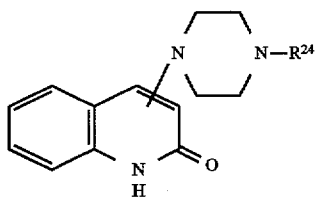

(6)

wherein $R^{24}$ is a hydrogen atom, a phenyl-lower alkyl group, a benzoyl-lower alkyl group, or a benzoyl group which may optionally have one to three lower alkoxy groups or a lower alkylenedioxy group on the phenyl ring thereof; and salts thereof; and (7) 6-[4-(3,4-Dimethoxybenzoyl)-1-1,2,3,4-tetrahydropirazyl]-3,4-dihydrocarbostyril and salts thereof;

Regarding the above compounds (1) to (6) and (7) (carbostyril derivatives) and the processes available for production thereof, the descriptions in the following literature can be consulted and are incorporated herein by reference: Japanese Patent Kokai Publication No. 83677/1983, No. 267556/1986, No. 230687/1988, No. 34963/1989, Synopsis of the 111st Congress of Pharmaceutical Society of Japan 29TD11-1 (published Mar. 5, 1991), Japanese Patent Kokai Publication No. 225357/1988, No. 29667/1984. It is also known that these carbostyril derivatives are of value as various drugs such as cardiotonics, antihypertensive drugs, antiinflammatory drugs, antiarrhythmic drugs, etc.

The inventor of this invention did further research into these compounds (1) to (7) and found that they have apoptosis regulating (inhibitory or promoting) activity which are hardly predictable from the hithertknown actions.

Meanwhile, it is said that two types of mechanism are involved in cell death. One is a classical type of cell death called necrosis. Morphologically, necrosis is characterized by marked swelling of mitochondria, swelling of cytoplasm and nuclear alteration, followed by cell destruction and autolysis. It occurs passively or incidentally. Tissue necrosis is generally caused by physical trauma to cells or a chemical poison, for instance.

Another type of cell death is called apoptosis (programmed cell death) [Kerr, J. F. R. and Wyllie, A. H., Br. J. Cancer, 265, 239 (1972)]. It is said that apoptosis can occur under various physiological conditions. Morphologically, apoptosis is characterized by loss of contact with neighboring cells, concentration of cytoplasm, endonuclease activity-associated chromatin condensation and pyknosis, and segmentation of the nucleus, among others. Disappearance of microvilli from the cell surface and smoothening of the cell surface (vesicle formation on the cell surface: membrane blebbing) are also observed. Fragmentation of the nucleosome unit of DNA into DNA fragments 180-200 bases in size due to endonuclease activation is further observable. Final fragments of apoptotic body cells are phagocytosed by neighboring cells. This is the mechanism discussed by Duvall and Wyllie [Duvall, E. and Wyllie, A. H., Immunology Today, 7 (4), 115–119 (1986); Science, 245, 301–305 (1989)]. Wyllie further reported that glucocorticoid-induced apoptosis of thymocytes involves intracellular endonuclease activation [Wyllie, A. H., Nature, 284, 555–556 (1986)]. Endonuclease activity causes fragmentation, to the oligonucleotide level, of DNA in cells undergoing apoptosis and this can be readily confirmed by agarose gel electrophoresis.

Apoptosis can be considered as preprogrammed cell death seen in the process of development, differentiation, or turnover of tissues [Wyllie, A. H., et al., Int. Rev. Cytol., 68, 251–306 (1980)].

In thymocytes, an increase in calcium level in the calcium ionophore or an increase in cAMP level leads to promotion of that DNA fragmentation which is characteristic of the above-mentioned apoptosis [Wyllie, A. H. et al., J. Pathol., 142, 67–77 (1984)] and, therefore, it is supposed that the calcium ion and/or cAMP be involved in the mechanisms of apoptosis. As an example so far reported, there may be mentioned apoptosis of HL-60 cells whose differentiation is induced by retinoic acid or the calcium ionophore [Martin, S. J., et al., J. Immunol., 145, 1859–1867 (1990); Martin, S. J. et al., Clin. Exp. Immunol., 79, 448–453 (1990)].

Reportedly, apoptosis not only occurs upon physiological cell death in the process of embryogenesis and physiological death of normal cells in active cell cycle (e.g. liver, adrenal cortex and prostate cells) but also is induced by glucocorticoid treatment, cell injury by cytotoxic T cells, atrophy of hormone-dependent tissues, irradiation, NK cells, killer cells, tumor necrosis factor (TNF), lymphotoxin (LT), other cytokines, etc. [Wyllie, A. H. et al., Int. Rev. Cytol., 68, 251 (1980); Duvall, E. and Wyllie, A. H., Immunology Today, 7, 115–119 (1986); Sellins, K. S., et al., J. Immunol., 139, 3199 (1987); Yamada, T., et al., Int. J. Radiat. Biol., 53, 65 (1988); Wyllie, A. H., Nature, 284, 555 (1980); Schmid, D. S., et al., Proc. Natl. Acad. Sci. USA, 83, 1881–1885 (1986); John, C., et al., J. Immunol., 129 (4), 1782–1787 (1982); Howell, D. M., et al., J. Immunol., 140, 689–692 (1988); Gillian, B., et al., Eur. J. Immunol., 17, 689–693 (1987)]. In addition, apoptosis is also inducible by some antibodies, for example anti-CD3, anti-APO-I, and anti-Fas antibodies [Trauth, B.C., et al., Science, 245, 301–305 (1989); Smith, C. A., et al. Nature, 337, 181–184 (1989); Tadakuma, T., et al., Eur. J. Immunol., 20, 779 (1990)] and, further, apoptosis has been confirmed in the findings of Nakamura et al. as obtained in spontaneous regression of malignant tumor [Nakamura, Y., et al., Rinsho Hifuka (Jpn, J. Clin, Dermatol.), 35 (4), 289–295 (1981)].

On the other hand, actinomycin D (an RNA synthesis inhibitor), cycloheximide (a protein synthesis inhibitor) and calcium ion ($Ca^{2+}$) chelating agents, among others, have been reported as being capable of repressing apoptosis and, in addition, cyclosporin A (an immuno-suppressant), hematopoietic system cytokines [IL-3, GM-CSF (granulocyte macrophage colony stimulating factor), G-CSF (granulocyte colony stimulating factor)], IL-2, bcl-2 gene product, and the like can reportedly repress apoptosis [Cohen, J. J., J. Immunol., 132, 38 (1984); Wyllie, A. H., et al., J. Pathol., 142, 67 (1984); Shi, Y., et al., Nature, 339, 625 (1989); Williams, G. L., et al., Nature, 343, 76 (1990); Nielo, M. A., J. Immunol., 143, 4166 (1989); Vaux, D. L., et al., Nature, 335, 1440 (1988)]. However, for cycloheximide and actinomycin D, there is a report describing apoptosis induction in acute leukemia cells by cycloheximide, in small intestine crypt cells by actinomycin D, and in HL-60 cells by both [Martin, S. J., et al., J. Immunol., 145, 1859–1867 (1990)]. On the other hand, it is reported that cycloheximide rather suppresses, and actinomycin D potentiates, apoptosis of the lymphocytic tumor cells which are present before X-ray radiation and are increased by X-ray radiation. Therefore, it is suggested that the kind of cells, conditions, and other mechanisms be involved in the suppression or promotion of apoptosis [Igarashi, T., et al., Nippon Ketsueki Gakkaishi (Acta Hematol. Jpn.), 51 (2), 144 (1988)]. At any rate, it is currently considered that the differentiation, growth and maturation of cells are closely associated with apoptosis and that substances capable of playing some or other part in such cell differentiation, growth or the like are associated with apoptosis as well.

Recently, cancer treatment with anti-Apo-I anti-body has been attempted as an apoptosis-related therapy. Among the myelodysplastic syndrome (MDS), refractory anemia (RA) and refractory anemia with ring sideroblast (RARS) in which pancytopenia is predominant should preferably be treated with a combination of retinoic acid or active-type vitamin $D_3$, which is a differentiation inducer for hemopoietic cells, and GM-CSF or IL-3 as an apoptosis regulating agent which suppresses excessive apoptosis of platelet producing cells whereas, in RAEB (refractory anemia with excess of blasts) and RAEB-t (RAEB in transformation) in which blast cell growth is active, retinoic acid and active type vitamin $D_3$ are said to act as differentiation inducing agents, which induce differentiation of hemopoietic cells into blast cells, and etoposide and aclarubicin are said to act as apoptosis regulating agents, which suppress blast cell growth (thereby promote apoptosis) [Shibuya, T., J. Clin. Exp. Med., 160 (5), 319–323 (1992)].

Murakami et al. reported that about half of transgenic mice expressing anti-erythrocyte autoantibody manifest autoimmune diseases as a result of loss of self tolerance and that this is due to deficiency in ability to eliminate autoantibodies producing cells as resulting from apoptosis induction by self antigen-autoantibody producing cells reactions as in normal mice [Murakami, M., et al., Nature, 357, 77–80 (1992)].

Watanabe-Fukunaga et al. suggest that, for MRL lpr/lpr mice, Fas moleculs relating to apoptosis has abnormality and the negative selection (apoptosis) mechanism of autoreactive T-cells does not work properly in thymus. Consequently, autoimmune diseases occur [Watanabe-Fukunaga, R., et al., Nature, 356, 314–317 (1992)].

According to Montagnier et al., apoptotic DNA bands are observed in T lymphocyte extracts from HIV-infected patients. This phenomenon is observed in 90% of asymptomatic HIV-infected patients and in 100% of AIDS patients and of ARC (AIDS-related complex) patients, indicating increased apoptosis induction in HIV-infected patients as well [Montagnier, L., et al., Sixieme Colloque des Cent Gardes, 9–17 (1991)].

As regards development stage cell death in chickens, administration in advance of NGF (nerve growth factor; a protein that promotes cell hypertrophy and nerve fiber elongation in the nerve cell ganglion) can result in complete inhibition of nerve cell death in that development stage [Hamburger, V., et al., J. Neurosci., 1, 60 (1981)] while administration of an antibody to NGF conversely leads to loss of about 90% of juvenile sympathetic nerve cells [Levi-Montalchini, R. and Booker, B., Proc. Natl. Acad. Sci. USA, 46, 384 (1960)].

Clark classified spontaneous neuronal deaths into three types and identified type I as apoptosis since, in type I neuronal death, morphological characteristics are identical with those in apoptosis and since type I cell death, together with DNA fragmentation, is involved in the cell death caused by deprivation of the growth factor [Clark, P. G. H., Anat. Embryol., 181, 195 (1990); J. Neurosci., 1, 60 (1981); Proc. Natl. Acad. Sci. USA, 46, 384 (1960); Rawson, C. L., et al., J. Cell. Biol., 113, 671 (1991)].

According to a report by Edwards et al., NGF can inhibit programmed death of sympathetic nerve cells, hence NGF can presumably control apoptosis [Edwards, S. N., et al., J. Neurochemistry, 57 (6), 2140–2143 (1991)].

According to Fischer et al., aged rats with learning disorder, when administered with NGF, can recover from learning disorder as a result of said NGF acting on forebrain basal field cholinergic nerve cells which are known to be found damaged in Alzheimer's disease [Fischer, W., et al., Nature, 329, 65 (1987); Barde, Y. -A., Neuron, 2, 1525 (1989); Hatanaka, H., Develop. Brain Res., 30, 47 (1986); Hatanaka, H., et al., Develop. Brain Res., 39, 85 (1988)]. Hatanaka et al. suggest the possibility that NGF can be effective in differentiation, maturation, life supporting and prevention of aging, protect nerve cells from damaging, promote recovery of damaged nerve cells and inhibit nerve cell death in nervous diseases associated with aging of the brain, in particular in Alzheimer's disease [Hatanaka, H., Taisha (Metabolism), 28, 891–899 (1991)].

For hepatic lesion of drug resistant virus hepatitis, acceleration of apoptosis which is direct or through the immune system, is considered to be involved in hepatic lesion [Bursh, W., et al., TIPS, 13, 245–251 (1992)].

On the other hand, it is known that, in the liver, mitogens induce the growth of hepatocytes to produce a hyperplastic state, and this state is normalized by falling off and necrosis, i.e. apoptosis, of hepatocytes [Kerr, J. F., et al., Br. J. Cancer, 26, 239–257 (1972)]. As far as the liver is concerned, apoptosis is observable in hepatic hyperplasia, hyperplastic tuberculation and hepatic cancer, among others [Columbano, A., et al., Lab. Invest., 52, 670–675 (1985); Columbano, A., et al., Am. J. Pathol., 1.16, 441–446 (1984)] while, according to Kerr et al., apoptosis is not accompanied by inflammation or fibroplasia [Kerr, J. F., et al., Lancet, 2, 827–828 (1979)]. In view of the reports cited above, the present inventors consider that patients with hepatitis, whether acute or chronic, may be cured when apoptosis is inhibited. They further consider that, in patients in the process of transition from chronic hepatitis to hepatic cirrhosis and further to hepatic cancer, apoptosis is in a controlled state and thus cytotoxic T cells can induce hepatocyte inflammation, followed by fibrosis, causing aggravation to hepatic cirrhosis and that, therefore, hepatitis might be suppressed and development into cirrhosis prevented when apoptosis is promoted.

The present invention provides an apoptosis. regulating composition comprising, as an active ingredient, an effective amount of at least one of the compounds (1)–(7) and salts thereof in combination with a pharmacologically acceptable carrier therefor.

The apoptosis regulating composition of this invention can regulate or control apoptosis and, because of this action, can. be suitably used in the treatment of various diseases, as mentioned hereinbefore. Specifically stated, the apoptosis regulating composition of the invention can be used in the treatment of, for example, cancer; retrovirus-related diseases including AIDS, ARC (AIDS related complex), ATL (adult T cell leukemia), hairy cell leukemia, myelopathy (HAM/TSP), respiratory disorder (HAB/HABA), arthropathy (HAAP), HIV- or HTLV-I (human T cell leukemia virus type I)-related diseases such as uveitis (HAU), and C-type hepatitis; autoimmune diseases including collagen diseases such as SLE (systemic lupus erythematosus) and rheumatoid arthritis (RA), ulcerative colitis, Sjögren's syndrome, primary biliary hepatic cirrhosis, idiopathic thrombocytopenic purpura (ITP), autoimmune hemolytic anemia, maysthenia gravis, Hashimoto's disease and insulin dependent (type I) diabetes mellitus; diseases accompanied by thrombocytopenia, for example, myelodysplastic syndrome (MDS), periodic thrombocytopenia, aplastic anemia, idiopathic thrombocytopenia and disseminated intravascular coagulation; liver diseases such as viral or drug-induced hepatitis (such as types C, A, B, and F) and hepatic cirrhosis; Alzheimer's disease and senile dementia of Alzheimer type; myocarditis; ARDS (adult respiratory distress syndrome);

infectious diseases; prostatic hypertrophy; uterine myoma; bronchial asthma; arteriosclerosis; congenital malformations; nephritis; senile cataract; chronic fatigue syndrome (CFS); and myotonic dystrophy.

The groups in the respective general formulas representing said compounds (1) to (6) are as follows.

The halogen atom means a fluorine, chlorine, bromine or iodine atom.

The lower alkylenedioxy group may for example be a straight- or branched-chain $C_{1-4}$ alkylenedioxy group such as methylenedioxy, ethylenedioxy, trimethylenedioxy, tetramethylenedioxy and so on.

The benzoyl group which may have 1 to 3 substituents selected from the class consisting of lower alkoxy, halogen, lower alkyl, lower alkanoylamino and Lower alkylthio groups or a lower alkylenedioxy group on its phenyl ring includes benzoyl groups optionally having 1 to 3 substituents selected from the class consisting of straight- or branched-chain $C_{1-6}$ alkoxy groups, halogen atoms, straight- or branched-chain $C_{1-6}$ alkyl groups, straight- or branched-chain $C_{1-6}$ alkanoylamino groups and straight- or branched-chain $C_{1-6}$ alkylthio groups or a $C_{1-4}$ alkylenedioxy group on the phenyl ring, such as benzoyl, 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 4-iodobenzoyl, 3,5-dichlorobenzoyl, 2,6-dichlorobenzoyl, 3,4-dichlorobenzoyl, 3,4-difluorobenzoyl, 3,5-dibromobenzoyl, 3,4,5-trichlorobenzoyl, 2-methylbenzoyl, 3-methylbenzoyl, 4-methylbenzoyl, 2-ethylbenzoyl, 3-ethylbenzoyl, 4-ethylbenzoyl, 3-isopropylbenzoyl, 4-hexylbenzoyl, 3,4-dimethylbenzoyl, 2,5-dimethylbenzoyl, 3,4,5-trimethylbenzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 4-hexyloxybenzoyl, 3,4-dimethoxybenzoyl, 3,4-diethoxybenzoyl, 3,4,5-trimethoxybenzoyl, 2,5-dimethoxybenzoyl, 3,4-methylenedioxybenzoyl, 3,4-ethylenedioxybenzoyl, 2,3-methylenedioxybenzoyl, 3-methyl-4-chlorobenzoyl, 2-chloro-6-methylbenzoyl, 2-methoxy-3-chlorobenzoyl, 2-methylthiobenzoyl, 3-methylthiobenzoyl, 4-metylthiobenzoyl, 2-ethylthiobenzoyl, 3-ethylthiobenzoyl, 4-ethylthiobenzoyl, 3-isopropylthiobenzoyl, 4-hexylthiobenzoyl, 3,4-dimethylthiobenzoyl, 2,5-dimethylthiobenzoyl, 3,4,5-trimethylthiobenzoyl, 2-formylaminobenzoyl, 3-acetylaminobenzoyl, 4-acetylaminobenzoyl, 2-acetylaminobenzoyl, 3-propionylaminobenzoyl, 4-butyrylaminobenzoyl, 2-isobutyrylaminobenzoyl, 3-pentanoylaminobenzoyl, 3-tert-butylcarbonylaminobenzoyl, 4-hexanoylaminobenzoyl, 2,6-diacetylaminobenzoyl and so on.

The lower alkyl group includes straight- or branched-chain $C_{1-6}$ alkyl groups such as methyl, ethyl, propyl, isopropyl, butyl, tert-butyl, pentyl, hexyl and so on.

The phenyl-lower alkyl group includes phenylalkyl groups whose alkyl moietieS are straight- or branched-chain $C_{1-6}$ alkyl groups, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl and so on.

The amino group which may have a lower alkanoyl group includes amino groups optionally having straight- or branched-chain $C_{1-6}$ alkanoyl groups, such as amino, formylamino, acetylamino, propionylamino, butyrylamino, isobutyrylamino, pentanoylamino, tert-butylcarbonylamino, hexanoylamino and so on.

The lower alkylthio group includes straight- or branched-chain $C_{1-6}$ alkylthio groups, such as methylthio, ethylthio, propylthio, isopropylthio, butylthio, tert-butylthio, pentylthio, hexylthio and so on.

The lower alkanoyloxy group includes straight- or or branched-chain $C_{1-6}$ alkanoyloxy groups such as formyloxy, acetyloxy, propionyloxy, butyryloxy, isobutyryloxy, pentanoyloxy, tert-butylcarbonyloxy, hexanoyloxy and so on.

The lower alkanoyl group includes straight- or branched-chain $C_{1-6}$ alkanoyl groups such as formyl, acetyl, propionyl, butyryl, pentanoyl, hexanoyl and so on.

The phenyl-lower alkyl group having lower alkanoyloxy or hydroxy groups as substituents on the phenyl ring includes phenylalkyl groups which have 1 to 3 straight- or branched-chain $C_{1-6}$ alkanoyloxy or hydroxy groups as substituents on the phenyl ring and whose alkyl moieties are straight- or branched-chain $C_{1-6}$ alkyl groups, such as 2-, 3- or 4-hydroxybenzyl, 2-(3,4-dihydroxyphenyl)ethyl, 1-(3,4-dihydroxyphenyl)ethyl, 2-(3-hydroxyphenyl)ethyl, 3-(4-hydroxyphenyl)propyl, 6-(3,4-dihydroxyphenyl)hexyl, 3,4-dihydroxybenzyl, 3,4,5-trihydroxybenzyl, 2-formyloxybenzyl, 3-acetyloxybenzyl, 3-(2-acetyloxyphenyl)propyl, 4-(4-acetyloxyphenyl)butyl, 2-popionyloxybenzyl, 3-(3-butyryloxyphenyl)propyl, 4-(4-isobutyryloxyphenyl)butyl, 5-(2-tert-butylcarbonyloxyphenyl)pentyl, 6-(3-pentanoyloxyphenyl)hexyl, (2,4-diacetyloxy)benzyl and so on.

The lower alkoxy group includes straight- or branched-chain $C_{1-6}$ alkoxy groups such as methoxy, ethoxy, propoxy, isopropoxy, butoxy, tert-butoxy, pentyloxy, hexyloxy and so on.

The benzoyl group which may have lower alkoxy groups as substituents on the phenyl ring includes benzoyl groups having 1 to 3 straight- or branched-chain $C_{1-6}$ alkoxy groups substituting the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 3-isopropoxybenzoyl, 4-butoxybenzoyl, 2-pentyloxybenzoyl, 3-hexyloxybenzoyl, 3,4-dimethoxybenzoyl, 2,5-dimethoxybenzoyl, 3,4,5-trimethoxybenzoyl and so on.

The lower alkyl group which may have a hydroxy group includes, in addition to the above-mentioned unsubstituted lower alkyl groups, straight- or branched-chain $C_{1-6}$ alkyl groups having a hydroxy group, such as hydroxymethyl, 2-hydroxyethyl, 1-hydroxyethyl, 3-hydroxypropyl, 2-hydroxybutyl, 1-hydroxypropyl, 4-hydroxybutyl, 1,1-dimethyl-2-hydroxyethyl, 5-hydroxypentyl, 6-hydroxyhexyl, 1-hydroxyisopropyl, 2-methyl-3-hydroxypropyl and so on.

The lower alkenyl group includes straight- or branched-chain $C_{2-6}$ alkenyl groups such as vinyl, allyl, 2-butenyl, 3-butenyl, 1-methylallyl, 2-pentenyl, 2-hexenyl and so on.

The lower alkanesulfonyl group includes sulfonyl groups having a straight- or branched-chain $C_{1-6}$ alkyl group, such as methanesulfonyl, ethanesulfonyl, propanesulfonyl, isopropanesulfonyl, butanesulfonyl, tert-butanesulfonyl, pentanesulfonyl, hexanesulfonyl and so on.

The lower alkoxycarbonyl group includes carbonyl groups having a straight- or branched-chain $C_{1-6}$ alkoxy group, such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and so on.

The phenyl-lower alkyl group which may have 1 to 3 substituents selected from the class consisting of lower alkoxy groups, lower alkyl groups and halogens on the phenyl ring includes, in addition to the phenyl-lower alkyl groups mentioned hereinabove, straight- or branched-chain $C_{1-6}$ alkyl groups having a phenyl group optionally having 1 to 3 substituents selected from the class consisting of straight- or branched-chain $C_{1-6}$ alkoxy groups, straight- or branched-chain $C_{1-6}$ alkyl groups, and halogens on the phenyl ring, such as 2-chlorobenzyl, 2-(3-chlorophenyl) ethyl, 1-(4-chlorophenyl)ethyl, 3-(2-fluorophenyl)propyl, 4-(3-fluorophenyl)butyl, 1,1-dimethyl-2-(4-fluorophenyl) ethyl, 5-(2-bromophenyl)pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl) ethyl, 5-(3,5-dibromophenyl)pentyl, 6-(3,4,5-trichlorophenyl)hexyl, 4-methylbenzyl, 2-(2-methylphenyl) ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4-hexyloxyphenyl)ethyl, 2-methyl-3-(3,4-di-methoxyphenyl)propyl, 2-(3,4-dimethoxyphenyl)ethyl, 2-(3,4-diethoxyphenyl)ethyl, 2-(3,4-diethoxyphenyl)ethyl, 2-(3,4,5-trimethoxyphenyl)ethyl, 1-(2,5-dimethoxyphenyl) ethyl and so on.

The benzoyl group which may have substituents selected from the class consisting of amino groups, which may be substituted by a lower alkyl group, and hydroxy groups on the phenyl ring includes benzoyl groups optionally having 1 to 3 substituents selected from the class consisting of amino groups, which may have 1 or 2 straight- or branched-chain $C_{1-6}$ alkyl groups, and hydroxy groups on the phenyl ring, such as benzoyl, 2-3- or 4-aminobenzoyl, 2,4-diaminobenzoyl, 2-, 3- or 4-hydroxybenzoyl, 3,4-dihydroxybenzoyl, 2,3-dihydroxybenzoyl, 2,4-dihydroxybenzoyl, 2,6-dihydroxybenzoyl, 3,5-dihydroxybenzoyl, 2,5-dihydroxybenzoyl, 3,4,5-trihydroxybenzoyl, 2,4,6-trihydroxybenzoyl, 2-, 3- or 4-dimethylaminobenzoyl, 2-methylaminobenzoyl, 3-ethylaminobenzoyl, 4-propylaminobenzoyl, 2-isopropylaminobenzoyl, 3-n-butylaminobenzoyl, 4-tert-butylaminobenzoyl, 2-pentylaminobenzoyl, 3-hexylaminobenzoyl, 4-dipentylaminobenzoyl, 2-methyl-n-butylaminobenzoyl, 3,5-di(dimethylamino)benzoyl and so on.

The piperazinyl group which may have a lower alkyl group in the 4-position of a piperazine ring includes piperazinyl groups optionally having a straight- or branched-chain $C_{1-6}$ alkyl group in the 4-position of the piperazine ring, such as piperazinyl, 4-methyl-1-piperazinyl, 4-ethyl-1-piperazinyl, 4-propyl-1-piperazinyl, 4-butyl-1-piperazinyl, 4-tert-butyl-1-piperazinyl, 4-pentyl-1-piperazinyl, 4-hexyl-1-piperazinyl and so on.

The benzoyl group which may have 1 to 3 lower alkoxy groups or a lower alkylenedioxy group on the phenyl ring includes benzoyl groups optionally having 1 to 3 $C_{1-6}$ alkoxy groups or a $C_{1-4}$ alkylenedioxy group on the phenyl ring, thus including, in addition to the groups mentioned above for the benzoyl group which may have lower alkoxy groups substituting the phenyl ring, 3,4-methylenedioxybenzoyl, 3,4-ethylenedioxy benzoyl, 2,3-methylenedioxybenzoyl, 3,4-trimethylenedioxybenzoyl, 2,3-tetramethylenedioxybenzoyl and so on.

The $C_{1-6}$ alkyl group includes straight- or branched-chain alkyl groups of 1 to 16 carbon atoms, such as methyl, ethyl, propyl, isopropyl, butyl, tert-butyl, pentyl, hexyl, heptyl, octyl, nonyl, decyl, undecyl, dodecyl, tridecyl, tetradecyl, pentadecyl, hexadecyl and so on.

The lower alkynyl group includes straight- or branched-chain alkynyl groups of 2 to 6 carbon atoms, such as ethynyl, propargyl, 2-butynyl, 1-methyl-2-propargyl, 2-pentynyl, 2-hexynyl and so on.

The lower alkoxycarbonyl-lower alkyl group includes alkoxycarbonylalkyl groups having 1 to 6 carbon atoms in its alkoxy moiety and 1 to 6 carbon atoms in its alkyl moiety, such as methoxycarbonylmethyl, 3-methoxycarbonylpropyl, 4-ethoxycarbonylbutyl, 6-propoxycarbonylhexyl, 5-isopropoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl, hexyloxycarbonylmethyl and so on.

The lower alkanoylamino group includes straight- or branched-chain $C_{1-6}$ alkanoylamino groups such as formylamino, acetylamino, propionylamino, butyrylamino, isobutyrylamino, pentanoylamino, tert-butylcarbonylamino, hexanoylamino and so on.

The amino group which may be substituted by a lower alkyl group includes amino groups optionally having 1 or 2 straight- or branched-chain $C_{1-6}$ alkyl groups, such as amino, methylamino, ethylamino, propylamino, isopropylamino, n-butylamino, tert-butylamino, pentylamino, hexylamino, dimethylamino, diethylamino, dipropylamino, diisopropylamino, di-n-butylamino, dipentylamino, dihexylamino, methylethylamino, methylpropylamino, methyl-n-butylamino, ethylpentylamino, propylhexylamino and so on.

The phenyl-lower alkoxycarbonyl-lower alkyl group includes phenylalkoxycarbonylalkyl groups having 1 to 6 carbon atoms in its alkoxy moieties and alkyl moieties, such as phenylmethoxycarbonylmethyl, 2-(2-phenylethoxycarbonyl)ethyl, 1-(1-phenylethoxycarbonyl) ethyl, 3-(3-phenylpropoxycarbonyl)propyl, 4-(4-phenylbutoxycarbonyl)butyl, 1,1-dimethyl-2-(2-phenylethoxycarbonyl)ethyl, 5-(5-phenylpentyloxycarbonyl)pentyl, 6-(6-phenylhexyloxycarbonyl)hexyl, 2-methyl-3-(3-phenylpropoxycarbonyl)propyl and so on.

The benzoyl-lower alkyl group includes $C_{1-6}$ alkyl groups having a benzoyl group as a substituent, such as benzoylmethyl, 2-benzoylethyl, 2-benzoylpropyl, 3-benzoylpropyl, 1-methyl-2-benzoylethyl, 2-benzoylbutyl, 3-benzoylbutyl, 4-benzoylbutyl, 1,1-dimethyl-2-benzoylbutyl, 2-benzoylpentyl, 3-benzoylpentyl, 4-benzoylhexyl and so on.

The amido-lower alkyl group which may be substituted by a lower alkyl group includes amidoalkyl groups whose alkyl moieties are straight- or branched-chain $C_{1-6}$ alkyl groups and which may have 1 to 2 straight- or branched-chain $C_{1-6}$ alkyl groups as substituents, such as amidomethyl, methylamidomethyl, 2-ethylamidoethyl, 1-propylamidoethyl, 3-isopropylamidopropyl, 4-butylamidobutyl, 1,1-dimethyl-2-tert-butylamidoethyl, 5-pentylamidopentyl, 6-hexylamidohexyl, 2-dimethylamidoethyl, diethylamidomethyl, 1-dipropylamidoethyl, 3-dibutylamidopropyl, 4-dipentylamidobutyl, 5-dihexylamidopentyl, 6-(N-methyl-N-ethylamido)hexyl, (N-ethyl-N-propylamido)methyl, 2-(N-methyl-N-butylamido)ethyl, 3-(N-methyl-N-hexylamido)propyl and so on.

Among the above-mentioned compounds (1) through (7) which can be used as the active ingredient in the present invention, the following compounds can be mentioned as particularly preferred species.

1-Benzyl-6-[4-(3,4-dimethoxybenzoyl)-1-piperazinyl]-3, 4-dihydrocarbostyril and its salt 6-[4-(3,4-dimethoxybenzoyl)-1-(1,2,3,4-tetrahydropyrazyl)]-3,4-dihydrocarbostyril and its salt The above active ingredient compounds can be easily converted to pharmaceutically acceptable salts with ordinary acids and these salts can be used as active compounds in the same manner as the free compounds. The acids mentioned above include inorganic acids such as sulfuric acid, nitric acid, hydrochloric acid, hydrobromic acid, etc. and organic acids such as acetic acid, p-toluenesulfonic acid, ethanesulfonic acid, oxalic acid, maleic acid, fumaric acid, citric acid, succinic acid, benzoic acid and so on.

The active ingredient compounds (1) through (7), inclusive of salts thereof, according to the present invention can be generally formulated into the per se conventional pharmaceutical preparations. Such preparations are prepared using the conventional fillers, extenders, binding agents, moistening agents, disintegrating agents, surfactants, lubricants, and like diluents or excipients. These pharmaceutical preparations may have various dosage forms selected according to the purposes of therapy, and typical examples thereof are tablets, pills, powders, solutions, suspensions, emulsions, granules, capsules, suppositories, injections (solutions, suspensions, etc.) and eye-drops.

For the manufacture of tablets, a wide variety of carriers so far well known in this field can be used. Thus, use can be made of, for example, vehicles or excipients such as lactose, sucrose, sodium chloride, glucose, urea, starch, calcium carbonate, kaolin, crystalline cellulose and silicic acid; binding agents such as water, ethanol, propanol, simple syrup, glucose solution, starch solution, gelatin solution, carboxymethylcellulose, shellac, methylcellulose, potassium phosphate and polyvinylpyrrolidone; disintegrating agents such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose; disintegration inhibitors such as sucrose, stearin, cacao butter and hydrogenated oils; absorption promoters such as quaternary ammonium bases and sodium lauryl sulfate; wetting agents or humectants such as glycerol and starch; adsorbents such as starch, lactose, kaolin, bentonite and colloidal silica; and lubricants such as refined talc, stearic acid salts, powdered boric acid and polyethylene glycol. When necessary, the tablets may further be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well known in the art can be used. Examples are vehicles or excipients such as glucose, lactose, starch, cacao butter, hardened vegetable oils, kaolin and talc; binding agents such as powdered gum arabic, powdered tragacanth gum, gelatin and ethanol; and disintegrating agents such as laminaran and agar.

For the manufacture of suppositories, a wide variety of carriers so far known can be used. As examples, there may be mentioned polyethylene glycol, cacao butter, higher alcohols, higher alcohol esters, gelatin and semisynthetic glycerides.

In preparing injections, the solutions or suspensions are preferably sterilized and are preferably isotonic with blood and, for preparing such dosage forms, all the diluents in conventional use in this field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc.

Furthermore, when necessary, the pharmaceutical preparations may contain coloring matters, preservatives, perfumes, flavoring agents, sweetening agents and the like as well as other drugs.

The proportion of the active ingredient compound in these pharmaceutical preparations of this invention is not critical but may suitably be selected in a wide range. Generally, however, the proportion is recommendably selected within the range of about 1 to about 70% by weight, preferably about 1 to about 30% by weight.

The route of administration of these pharmaceutical preparations of this invention is not critical, either, but is selected according to the dosage form, the patient's age, sex and other factors and the severity of the disease to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parenteral infusion containing glucose, amino acids and so on. Where necessary, these solutions may also be administered as it is by the intramuscular, intradermal, subcutaneous or intraperitoneal route. Suppositories are administered rectally. Of course, eye-drops are instilled into the eye.

While the dosage of the above pharmaceutical preparations is dependent on the method of administration, the patient's age, sex and other background factors, severity of the disease and so on, it is generally recommended to administer about 0.01 to 30 mg, as the active ingredient, viz. compound (1) through (7), per kilogram body weight per day. The amount of the active ingredient to be contained in each dosage unit is about 10 to 1000 mg.

The apoptosis regulating composition of the present invention has, in addition to the apoptosis regulating ability, the cell differentiation-inducing activity, cancer cell growth inhibitory activity, anticancer activity, antiretrovirus activity, life-prolonged effect activity against shock death from endotoxin, cytokine production inhibitory activity and peripheral lymphocyte activation inhibitory activity. Based on these activities, the apoptosis regulating composition of the present invention can be effectively used as, for example, an anticancer agent, cancer metastasis-inhibitory agent, therapeutic agent for thrombocytopenia, therapeutic or prophylactic agent for Alzheimer's diseases and for liver diseases, antiretrovirus agent, cytokine production inhibitory agent and immunosuppression agent.

The apoptosis regulating composition of the present invention, when administered as an anticancer composition, for instance, induces differentiation of cancer cells, subsequently promotes or inhibits apoptosis induction or, directly promotes or inhibits apoptosis induction, and thereby produces an anticancer effect. In this case, the composition of the invention, irrespective of dosage form and/or route of administration, can be used in combination with one or more of various anticancer agents known as cancer chemotherapeutic agents and/or radiation therapy. The active ingredient compound of the invention which can produce an excellent anticancer effect can thus markedly promote the effect of the other anticancer agent or agents combinedly used, to produce a synergistic effect. Therefore, even when the partner anticancer agent or agents are used in doses much smaller than the usual doses, a satisfactory anticancer effect can be obtained, whereby the adverse effects of the partner anticancer agent or agents can be minimized. As such chemotherapeutic agents, there may be mentioned, for example, 5-fluorouracil (5-FU; Kyowa Hakko Kogyo), mitomycin C (Kyowa Hakko Kogyo), futraful (FT-207; Taiho Pharmaceutical), endoxan (Shionogi & Co.) and toyomycin (Takeda Chemical Industries).

When used in the treatment of thrombocytopenia, the apoptosis regulating composition of the invention can produce a cell differentiation induction promoting action and at the same time an apoptosis suppressing action in patients with MDS such as RA or RARS, thus stimulating proliferation of hemopoietic cells and causing normal differentiation and maturation. In patients with MDS such as RAEB or RAEB-t, administration of the composition of the invention can result in induced differentiation of blast cells and inhibition of blast cell multiplication, whereby proliferation of mature cells can be caused. The composition of the invention can further be expected to act on promegakaryocytes and megakaryocytes and promote their differentiation and maturation, thereby promoting thrombopoiesis. For use in the treatment of thrombocytopenia, the apoptosis regulating composition of the invention can be used in combination with one or more other known drugs such as thrombopoiesis promoting agents to potentiate these partner drugs. Thus, in some instances, even when the partner drugs are used in fairly reduced doses, a satisfactory therapeutic effect can be produced and the adverse effects of said drugs can be thereby reduced.

The apoptosis regulating composition of the invention is useful also as a therapeutic and prophylactic agent for Alzheimer's disease. In this case, in patients with classical Alzheimer's disease or senile dementia of Alzheimer type, the composition of the invention exhibits an NGF-like action through inhibition of apoptosis, thus producing the above-mentioned therapeutic and prophylactic effects. Further, in that case, the composition of the invention can be used in combination with any of the conventional therapeutic agents for Alzheimer's disease such as cerebral circulation ameliorating agents and cerebral metabolic agents, whereby their effects can be promoted and their adverse effects reduced in some instances.

The apoptosis regulating composition of the present invention can be used as a cirrhosis preventive agent which controls apoptosis in patients with drug-induced hepatitis or viral hepatitis to thereby manifest a therapeutic effect in hepatitis and prevent hepatocytes from fibrogenesis.

The apoptosis regulating composition of the present invention has an antiretrovirus activity, and is useful as an antiretrovirus agent for the aforementioned retrovirus-related diseases such as HIV- or HTLV-I-related diseases and C-type hepatitis.

Further, the apoptosis regulating composition of the present invention is useful, based on its life-prolonged effect activity against shock death from endotoxin, as a therapeutic agent for various infectious diseases, especially septicemia.

Furthermore, the apoptosis regulating composition of the present invention has a peripheral lymphocyte activation inhibitory activity as is exhibited, for example, by cyclosporin A. The apoptosis regulating composition of the invention can be effectively used as an immunosuppression agent for the inhibition of rejection in organ transplant and for the treatment of the aforementioned various diseases, such as autoimmune diseases mentioned above, Behcet disease, sympathetic uveitis, psoriasis and the blood dyscrasia in which the immunological system is involved, such as aplastic anemia [Medical Immunology, 20: 77–83, 1990; Men'eki-yakuri (immunopharmacology), 8: 425–429, 1990; Igaku no ayumi, 151: 417–420, 421–424, 425–428, 1989; Pharmacological Reviews, 41: 259–371, 1989].

Moreover, the composition of the present invention, based on its cytokine production inhibitory activity, can be suitably used as a cytokine production inhibitory agent for the treatment of various diseases accompanied by abnormal production of cytokines, such as bacterial or viral infectious diseases [Igaku no ayumi, 159 (8): 467–470, 471–474, 1991], RA [Arthritis Rheum., 31,: 1041, 1988; Arthritis Rheum., 34: 1125, 1991; J. Immunol., 145: 4154, 1990; J. Immunol., 22: 1907, 1992; Bri. J. Rheum., 31: 293, 1992; Eur. J. Immunol., 18: 1797, 1989], ARDS [Nature, 324: 73, 1986], fluminant vital hepatitis [Lancet, ii: 72, 1986], CFS [Nippon Rinsho (Japan clinical medicine), 50 (11): 51–55, 1992; J. Infectious Diseases, 165: 994–1000, 1992], hyper-γ-globulinemia, intra-atrial myxoma and Castleman syndrome accompanied by increase of acute phase protein [Blood, 74: 1360, 1989; Eur. J. Immunol., 18: 1797, 1989], mesangial proliferative glomerulonephritis (PGS) [Chiryogaku (curative medicine), 24 (1); 49, 1990] and the aforementioned various autoimmune diseases and HIV- or HTLV-I-related diseases.

When used as an antitumor agent, the apoptosis regulating composition of the present invention is more effective which contains, as an active component, a test compound No.8 to be described later. For use as a therapeutic agent for autoimmune diseases, the composition of the invention is more effective which contains, as an active component, a test compound No. 16 or 31 to be described later. For use as an antiretrovirus agent, the composition of the invention is more effective which contains, as an active component, any of test compounds Nos. 2, 7, 8, 11, 25, 32 and 39 to be described later.

Some dosage form examples for the apoptosis regulating composition of the invention, and results of pharmaceutical studies on the active ingredient compounds are presented below.

Dosage Form Example 1

| | |
|---|---|
| 1-Benzyl-6-[4-(3,4-dimethoxybenzoyl)-1-piperazinyl]-3,4-dihydrocarbostyril | 150 g |
| Avicel (trademark, Asahi Chemical Industry Co., Ltd.) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Methanol | 40 g |

The above active ingredient compound, Avicel, corn starch and magnesium stearate are mixed and ground together and the resulting mixture is compression-molded with a dragee R10 mm punch. The tablets thus obtained are coated with a film coating composition consisting of hydroxypropylmethylcellulose, polyethylene glycol 6000, castor oil and methanol to give film-coated tablets.

Dosage Form Example 2

| | |
|---|---|
| 1-Benzyl-6-[4-(3,4-dimethoxybenzoyl)-1-piperazinyl]-3,4-dihydrocarbostyril | 150.0 g |

| | |
|---|---|
| Citric acid | 1.0 g |
| Lactose | 33.5 g |
| Dicalcium phosphate | 70.0 g |
| Pluronic F-63 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | q.s. |

The above active ingredient compound, citric acid, lactose, dicalcium phosphate, pluronic F-68 and sodium lauryl sulfate are admixed.

After size selection using a No. 60 screen, the mixture is granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, then dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

Pharmacological tests, described hereinafter, were performed using the following test compounds.

1. 6-[4-(4-Ethylbenzoyl)-1-piperazinyl]-3,4-dihydrocarbostyril
2. 8-Methyl-6-(1-piperazinyl)-3,4-dihydrocarbostyril
3. 6-[4-(3,4-Methylenedioxybenzoyl)-1-piperazinyl]-3,4-dihydrocarbostyril
4. 6-(4-Benzoyl-2-oxo-1-piperazinyl)-3,4-dihydrocarbostyril
5. 6-[4-(3,4-Dimethoxybenzoyl)-1-1,2,3,4-tetrahydropyrazyl]-3,4-dihydrocarbostyril
6. 6-(3-Oxo-1-piperazinyl)-3,4-dihydrocarbostyril
7. 6-[4-(4-Methylthiobenzoyl)-1-piperazinyl]-3,4-dihydrocarbostyril
8. 1-Benzyl-6-[4-(3,4-dimethoxybenzoyl)-1-piperazinyl]-3,4-dihydrocarbostyril
9. 6-[4-(4-Chlorobenzoyl)-1-piperazinyl]-3,4-dihydrocarbostyril
10. 6-[4-(3-Chlorobenzoyl)-1-piperazinyl]-3,4-dihydrocarbostyril
11. 1-(4-Hydroxybenzyl)-6-[4-(3,4-dimethoxybenzoyl)-1-piperazinyl]-3,4-dihydrocarbostyril
12. 1-(4-Acetyloxybenzyl)-6-[4-(3,4-dimethoxybenzoyl)-1-piperazinyl]-3,4-dihydrocarbostyril
13. 1-Benzoyl-6-[4-(3,4-dimethoxybenzoyl)-1-piperazinyl]-3,4-dihydrocarbostyril
14. 1-Naphthoyl-6-[4-(3,4-dimethoxybenzoyl)-1-piperazinyl]-3,4-dihydrocarbostyril
15. 8-Methoxy-6-[4-(3,4-dimethoxybenzoyl)-1-piperazinyl]-3,4-dihydrocarbostyril
16. 6-[4-(4-Methoxybenzyl)-1-piperazinyl]-3,4-dihydrocarbostyril
17. 6-[4-(4-Chlorobenzyl)-1-piperazinyl]-3,4-dihydrocarbostyril
18. 6-[4-(4-Methylbenzyl)-1-piperazinyl]-3,4-dihydrocarbostyril dihydrochloride
19. 6-[4-(3-Pyridylcarbonyl)-1-piperazinyl]carbostyril
20. 8-(1-Piperazinyl)-3,4-dihydrocarbostyril monohydrobromide
21. 4-[4-(3,4-Dimethoxybenzoyl)-1-piperazinyl]carbostyril
22. 3-[4-(3,4-dimethoxybenzoyl)-1-piperazinyl]carbostyril
23. 1-Allyl-5-[4-(3,4-dimethoxybenzoyl)-1-piperazinyl]-3,4-dihydrocarbostyril
24. 1-Acetyl-6-[4-(3,4-dimethoxybenzoyl)-1-piperazinyl]-3,4-dihydrocarbostyril
25. 1-(4-Hydroxybenzoyl)-6-[4-(3,4-dimethoxybenzoyl)-1-piperazinyl]-3,4-dihydrocarbostyril
26. 1-(3-Aminobenzoyl)-6-[4-(3,4-dimethoxybenzoyl)-1-piperazinyl]-3,4-dihydrocarbostyril
27. 1-Methyl-4-(1-piperazinyl)carbostyril monohydrochloride
28. 1-Benzyl-4-(1-piperazinyl)carbostyril monohydrochloride
29. 1-Hexadecyl-3-(4-methyl-1-piperazinyl)carbostyril oxalate
30. 1-Methyl-6-[4-(3,4-dimethoxybenzoyl)-1-piperazinyl]-3,4-dihydrocarbostyril
31. 1-Benzyl-3-(4-methyl-1-piperazinyl)carbostyril oxalate
32. 5-(4-Propargyl-1-piperazinyl)-3,4-dihydrocarbostyril
33. 5-[4-(4-Acetylaminobenzoyl)-1-piperazinyl]-3,4-dihydrocarbostyril
34. 4-(1-Piperazinyl)carbostyril monohydrochloride ¼ hydrate
35. 4-[4-(3,4-Methylenedioxybenzoyl)-1-piperazinyl]carbostyril
36. 3-(4-Benzyl-1-piperazinyl)carbostyril monohydrochloride ¼ hydrate
37. 3-[4-(2-Benzoylethyl)-1-piperazinyl]carbostyril
38. 1-Propargyl-6-[4-(3,4-dimethoxybenzoyl)-1-piperazinyl]-3,4-dihydrocarbostyril
39. 1-Ethoxycarbonyl-6-[4-(3,4-dimethoxybenzoyl)-1-piperazinyl]-3,4-dihydrocarbostyril
40. 1-Ethoxycarbonylmethyl-6-[4-(3,4-dimethoxybenzoyl)-1-piperazinyl]-3,4-dihydrocarbostyril
41. 1-(4-Dimethylaminobenzoyl)-6-[4-(3,4-dimethoxybenzoyl)-1-piperazinyl]-3,4-dihydrocarbostyril
42. 1-Benzyloxycarbonylmethyl-3-(4-methyl-1-piperazinyl)carbostyril oxalate
43. 1-Diethylamidomethyl-3-(4-methyl-1-piperazinyl)carbostyril
44. 1-Benzyl-5-[4-(3,4-dimethoxybenzoyl)-1-piperazinyl]-3,4-dihydrocarbostyril
45. 1-Benzyl-6-(4-benzoyl-1-piperazinyl)-3,4-dihydrocarbostyril
46. 1-Benzyl-6-[4-(2-methoxybenzoyl)-1-piperazinyl]-3,4-dihydrocarbostyril
47. 1-Benzyl-6-(4-benzyl-1-piperazinyl-3,4-dihydrocarbostyril dihydrochloride
48. 1-Benzyl-6-[4-(4-chlorobenzyl)-1-piperazinyl]-3,4-dihydrocarbostyril dihydrochloride
49. 1-Benzyl-6-[4-(3-methoxybenzyl)-1-piperazinyl]-3,4-dihydrocarbostyril
50. 1-Benzyl-6-[4-(4-bromobenzyl)-1-piperazinyl]-3,4-dihydrocarbostyril dihydrochloride
51. 1-Benzyl-6-[4-(4-methoxybenzyl)-1-piperazinyl]-3,4-dihydrocarbostyril 52. 1-Benzyl-6-[4-(4-fluorobenzyl)-1-piperazinyl]-3,4-dihydrocarbostyril dihydrochloride
53. 1-Benzyl-6-[4-(2-chlorobenzoyl)-1-piperazinyl]-3,4-dihydrocarbostyril
54. 1-Benzyl-6-[4-(4-n-butoxybenzoyl)-1-piperazinyl]-3,4-dihydrocarbostyril
55. 1-Benzyl-6-[4-(t-butylbenzoyl)-1-piperazinyl]-3,4-dihydrocarbostyril
56. 1-Benzyl-6-[4-(3,4-dichlorobenzoyl)-1-piperazinyl]-3,4-dihydrocarbostyril
57. 1-Benzyl-6-[4-2,4-dichlorobenzoyl)-1-piperazinyl]-3,4-dihydrocarbostyril
58. 1-Benzyl-6-[4-(4-chlorobenzoyl)-1-piperazinyl]-3,4-dihydrocarbostyril
59. 1-Benzyl-6-[4-(4-methylbenzyl)-1-piperazinyl]-3,4-dihydrocarbostyril dihydrochloride
60. 1-Benzyl-6-[4-(t-butylbenzyl)-1-piperazinyl]-3,4-dihydrocarbostyril fumalate
61. 1-Benzyl-6-[4-(4-methoxybenzyl)-1-piperazinyl]-3,4-dihydrocarbostyril dihydrochloride
62. 1-Benzyl-6-[4-(4-fluorobenzyl)-1-piperazinyl]-3,4-dihydrocarbostyril
63. 1-Benzyl-6-[4-(3-chlorobenzoyl)-1-piperazinyl]- 3,4-dihydrocarbostyril
64. 1-Benzyl-6-[4-(4-methylbenzyl)-1-piperazinyl]-3,4-dihydrocarbostyril
65. 1-Benzyl-6-[4-(3,4-dimethoxybenzyl)-1-piperazinyl]-3,4-dihydrocarbostyril dihydrochloride
66. 1-Benzyl-6-[4-(2,4-difluorobenzoyl)-1-piperazinyl]-3,4-dihydrocarbostyril
67. 1-Benzyl-6-[4-(4-ethylbenzoyl)-1-piperazinyl]-3,4-dihydrocarbostyril
68. 1-Benzyl-6-[4-(3,4-dimethylbenzyl)-1-piperazinyl]-3,4-dihydrocarbostyril dihydrochloride
69. 1-Benzyl-6-[4-(3,4-dimethylbenzoyl)-1-piperazinyl]-3,4-dihydrocarbostyril
70. 1-Benzyl-6-[4-(4-n-butoxylbenzyl)-1-piperazinyl]-3,4-dihydrocarbostyril dihydrochloride
71. 1-Benzyl-6-[4-(3,4-difluorobenzoyl)-1-piperazinyl]-3,4-dihydrocarbostyril dihydrochloride
72. 1-Benzyl-6-[4-(3,4-difluorobenzoyl)-1-piperazinyl]-3,4-dihydrocarbostyril
73. 1-Benzyl-6-[4-(4-bromobenzoyl)-1-piperazinyl]-3,4-dihydrocarbostyril
74. 1-Benzyl-6-[4-(4-n-butylbenzoyl)-1-piperazinyl]-3,4-dihydrocarbostyril
75. 1-Benzyl-6-[4-(3,4,5-trimethoxybenzoyl)-1-piperazinyl]-3,4-dihydrocarbostyril
76. 1-Benzyl-6-[4-(3,4-methylenedioxylbenzoyl)-1-piperazinyl]-3,4-dihydrocarbostyril;
77. 1-Benzyl-6-[4-(2,4-dimethoxylbenzoyl)-1-piperazinyl]-3,4-dihydrocarbostyril
78. 1-Benzyl-6-[4-(3,4,5-trimethoxylbenzyl)-1-piperazinyl]-3,4-dihydrocarbostyril dihydrochloride Pharmacological Test Example 1

(1) Apoptosis regulating efficacy test 1

This test was performed in accordance with the method described in the literature (Nicoletti, I., et al., J. Immunological Methods, 139, 271–279 (1991)).

CMK cells were suspended in RPMI-1640 medium supplemented with 10% fetal calf serum (FCS) at a concentration of $5 \times 10^4$ cells/ml and the test compound was added to the cell suspension at a concentration of 30 μg/ml. The system mixture was incubated in the wells of a 6-well microtiter plate (Costar) at 37° C. for 4 days. As a control, the vehicle alone was added to a similar suspension and the mixture was incubated in the same manner. After completion of cultivation, the cells were recovered and $1 \times 10^6$ cells were transferred into a polyethylene tube and centrifuged at 200×g for 5 minutes to provide a pellet.

The pellet obtained above was resuspended in 0.25 ml of buffer (50 μg/ml of propidium iodide (PI, Sigma, 100 μg/ml in PBS) in 0.1% sodium citrate (Wako Pure Chemical)+ 0.1% Triton X-100 (Katayama Kagaku). Prior to flow cytometric analysis, the tube was allowed to stand in the dark at 4° C. overnight.

The PI fluorescence of individual nucleus was determined by Profile II (Coulter) flow cytometer. For this purpose, a 488 nm argon laser was used at 1W. For focusing the red fluorescence of PI stained DNA, a 560 nm dichromic mirror DM570 and a 600 nm band-pass filter (bandwidth 35 nm) were used. Cell fragments were excluded from analysis by increasing the FACS threshold to an appropriate value. The proper threshold value has empirically selected.

The residual cell fragments show extremely low DNA red fluorescent emissions, while apoptic cells show a high SSC value owing to the concentration of nuclear chromatin. Therefore, these apoptic cells could be readily differentiated from the cell fragments. The flow velocity ratio was set at about 200 nuclei/second and each sample was analyzed for at least $10^4$ nuclei.

Cell fragments with low intensities of fluorescence were excluded by histogram analysis. Then, the ratio of the nuclei showing a content of not less than 2N to the nuclei showing a content of less than 2N was calculated. The nuclei showing a content of not less than 2N were regarded as nuclei having apoptic cells and the proportion of nuclei showing a content of less than 2N was regarded as fragmented DNA and used as an indicator of apoptosis inducing activity. The results obtained with the respective test compounds are shown in Table 1.

TABLE 1

| Test compound (30 μg/ml) | Number of viable cells (×10⁶/ well) | Fragmented DNA (%) | Test compound (30 μg/ml) | Number of viable cells (×10⁶/ well) | Fragmented DNA (%) |
| --- | --- | --- | --- | --- | --- |
| — | 2.00 | 12.7 | 21 | — | 40.1 |
| 1 | 0.80 | 39.9 | 22 | — | 80.3 |
| 2 | 1.45 | 17.6 | 23 | 0.65 | 64.0 |
| 3 | 1.20 | 28.2 | 24 | 0.70 | 45.1 |
| 4 | 1.92 | 15.8 | 25 | 1.62 | 24.8 |
| 5 | 0.15 | 81.6 | 26 | — | 79.9 |
| 6 | 2.53 | 26.1 | 27 | — | 67.6 |
| 7 | 0.47 | 33.0 | 29 | 0.08 | 73.0 |
| 8 | 0.10 | 71.3 | 30 | 0.40 | 73.2 |
| 9 | 0.77 | 34.0 | 31 | 0.32 | 57.7 |
| 10 | — | 15.2 | 32 | 2.28 | 17.5 |
| 11 | 0.62 | 71.4 | 33 | 1.55 | 20.3 |
| 12 | 0.62 | 73.2 | 34 | 1.15 | 20.2 |
| 13 | 0.82 | 40.3 | 35 | 0.05 | 76.6 |
| 14 | 0.08 | 65.2 | 36 | 0.57 | 31.1 |
| 15 | 0.05 | 55.7 | 37 | 0.12 | 69.4 |
| 16 | 0.80 | 45.9 | 38 | 0.93 | 48.7 |
| 17 | 0.03 | 74.2 | 39 | 1.42 | 23.9 |
| 18 | 0.08 | 76.8 | 40 | 1.08 | 31.8 |
| 19 | 2.17 | 12.9 | 41 | 0.43 | 78.8 |
| 20 | 1.75 | 27.6 | 42 | 0.40 | 63.4 |

(2) Apoptosis regulating efficacy test 2

An apoptosis regulating efficacy test for estimating the suppressive effect of each test compound on the inhibition of tumor growth by tumor necrosis factor (TNF) which is known to induce apoptosis was carried out using mouse LS cells in the following manner.

The mouse LS cell line used was a derivative strain of mouse connective tissue-derived fibroblast cell line L-929 established by Sanford et al. (Sanford, K. K., et al., J. Natl. Cancer Inst., 9, 229 (1948):ATCC CCL1).

The above L-929 cell line and its derivative LS cell line have been used in the assay of biological activity of TNF because the growth of these cells is inhibited by TNF (Yamazaki, S., et al., Japan J. Med. Sci. Bio., 39, 105–118 (1986)).

As the LS cell line, a high-TNF-sensitive cell line obtained by derivatizing said L-929 at Dainippon Pharmaceutical Co. (LS cell, Dainippon Pharmaceutical, Catalog No. 03-449) was used. As TNF, a recombinant human TNF-α constructed by expression in $E.\ coli$ (specific activity $2 \times 10^7$ U/mg, Genzyme) was used.

The wells of a 96-well microtiter plate were filled with 50 μl aliquots of Eagle's MEM medium supplemented with 10% fatal calf serum (FCS) and containing 40 U/ml of said TNF-α. Then, 50 μl aliquots of each test compound in a doubling dilution series (3.75–120 μg/ml) were added to the wells. Then, 100 μl aliqots of a suspension of mouse LS cells adjusted to a concentration of $7.5 \times 10^4$ cells/ml were added. (The above cells were incubated in 10% FCS-containing Eagle's MEM medium for 3–4 days beforehand and adjusted to $7.5 \times 10^4$ cells/ml). The plate was then incubated in the presence of 5% $CO_2$ at 37° C. for 3 days. The final concentration of TNF-α was 10 U/ml and the final concentration of each test compound was 0.938–30 μg/ml.

The cell culture in each well was subjected to MTT assay (J. immunol. Methods, 65, 55 (1983)) using the culture medium alone as the solvent, as follows.

MTT (3-(4,5-dimethyl-2-thiazolyl)-2,5-diphenyl-2H-tetrazolium bromide) reagent (Dojin Kagaku) was dissolved in PBS$^{(-)}$ (Nippon Pharmaceutical) at a concentration of 2.5 mg/ml and sterilized by filtration for use.

To the above plate was added 0.01 ml/well of a 2.5 mg/ml solution of MTT prepared above and the plate was incubated in the presence of 5% $CO_2$ at 37° C. for 3 hours. Then, 0.1 ml aliquots of 0.01N HCl solution containing 10% SDS were added to the wells and the plate was further incubated in the presence of 5% $CO_2$ at 37° C. overnight. The stained viable cells were determined for optical density (O.D.) at 580 nm using Titertec Multiskan (Titertek). In the above test, with the cell growth in the medium alone being taken as 100%, the addition of 10 U/ml of TNF-α resulted in 86.7% inhibition of cell growth.

The % growth of cells after addition of each test compound was determined and compared with the % growth value after addition of 10 U/ml of TNF-α to estimate how much each test compound antagonized the cell growth inhibitory activity of TNF-α.

The results are shown in Table 2.

Each percent (%) suppression value in the table represents (% growth after addition of each test compound) -(% growth after addition of TNF-α alone). Thus, the larger the value, the greater is the suppressive or antagonizing activity of the particular test compound against the cell growth inhibitory effect of TNF-α.

TABLE 2

| Test compound | Concentration (μg/ml) | Percent suppression (%) | Test compound | Concentration (μg/ml) | Percent suppression (%) |
|---|---|---|---|---|---|
| — | — | 0.0 | 20 | 7.5 | 5.8 |
| 1 | 7.5 | 19.8 | 23 | 7.5 | 16.0 |

TABLE 2-continued

| Test compound | Concentration (μg/ml) | Percent suppression (%) | Test compound | Concentration (μg/ml) | Percent suppression (%) |
|---|---|---|---|---|---|
| 2 | 7.5 | 10.7 | 25 | 7.5 | 22.1 |
| 3 | 7.5 | 0.9 | 29 | 1.875 | 9.1 |
| 4 | 7.5 | 8.6 | 30 | 7.5 | 16.0 |
| 5 | 7.5 | 37.4 | 31 | 7.5 | 18.6 |
| 6 | 7.5 | 7.3 | 32 | 7.5 | 17.6 |
| 7 | 7.5 | 9.9 | 33 | 7.5 | 7.4 |
| 8 | 7.5 | 28.0 | 34 | 7.5 | 13.1 |
| 11 | 7.5 | 15.9 | 35 | 0.938 | 8.2 |
| 12 | 7.5 | 11.1 | 36 | 7.5 | 24.8 |
| 13 | 7.5 | 18.0 | 38 | 7.5 | 20.8 |
| 14 | 7.5 | 14.4 | 39 | 7.5 | 9.8 |
| 16 | 7.5 | 17.3 | 40 | 7.5 | 9.4 |
| 17 | 1.875 | 6.5 | 41 | 7.5 | 23.8 |
| 18 | 7.5 | 3.2 | 42 | 7.5 | 18.5 |
| 19 | 7.5 | 6.0 | 43 | 7.5 | 7.2 |

Pharmacoloqical Test Example 2

Effect on human promyeocytic leukemia cells (HL-60)

HL-60 cells were suspended in RPMI-1640 medium supplemented with 10% FCS and incubated in the presence of 5% $CO_2$ at 37° C. to provide a suspension of $5 \times 10^5$ cells/ml.

Then, the wells of a 6-well microtitar plate (coaster) were filled with the above medium containing 30 μg/ml of the test compound and the plate was incubated in the presence of 5% $CO_2$ at 37° C. for 3 days. As a control group, the above medium alone was added and the plate was similarly incubated. After completion of culture, each cultured cell suspension was taken in an Eppendorff tube and stained with 0.2% trypan blue-containing phosphate buffer and the viable cells were counted using a hemocytometer.

The above cells were suspended at a concentration of $1 \times 10^7$ cells/ml. To 100 μl of this suspension was added 5 μl of fluorescein isothiocyanate (FITC)-labelled antihuman CD11b antibody (Mol, Coulter) and the reaction was carried out on ice in the dark for 30 minutes. The reaction mixture was then washed with 0.1% BSA (bovine serum albumin, Sigma)-containing PBS (phosphate buffer, Nissui Pharmaceutical) twice and finally suspended in 500 μl of a similar buffer. Then, the intensity of fluorescence was measured by Profile II (Coulter) flow cytometry. The results are shown in Tables 3 and 4.

TABLE 3

| Test compound | Induction of differentiation effect |
|---|---|
| 1 | 594 |
| 2 | 611 |
| 5 | 3215 |
| 7 | 274 |
| 8 | 31835 |
| 9 | 231 |
| 10 | 300 |
| 11 | 2654 |
| 12 | 1337 |
| 13 | 240 |
| 14 | 2902 |
| 15 | 11206 |
| 17 | 1024 |
| 18 | 635 |
| 21 | 214 |

TABLE 3-continued

| Test compound | Induction of differentiation effect |
|---|---|
| 22 | 322 |
| 23 | 1292 |
| 24 | 227 |
| 25 | 628 |
| 26 | 371 |
| 27 | 2995 |
| 28 | 360 |
| 29 | 3529 |
| 30 | 1615 |
| 31 | 527 |
| 35 | 1968 |
| 37 | 2206 |
| 38 | 304 |
| 41 | 1994 |
| 42 | 2221 |
| 43 | 199 |
| 44 | 2457 |
| 45 | 5900 |
| 46 | 7522 |
| 47 | 1618 |
| 48 | 17848 |
| 49 | 983 |
| 50 | 11704 |
| 51 | 12124 |
| 52 | 1697 |
| 53 | 2951 |
| 54 | 718 |
| 55 | 5463 |
| 56 | 26943 |
| 57 | 8138 |
| 58 | 760 |
| 59 | 35950 |
| 60 | 37120 |
| 61 | 16750 |
| 62 | 19242 |
| 63 | 6150 |
| 64 | 3260 |
| 65 | 13130 |
| 66 | 2570 |
| 67 | 4240 |
| 68 | 117680 |
| 69 | 41520 |
| 70 | 84110 |
| 71 | 31210 |
| 72 | 1160 |
| 73 | 860 |
| 74 | 7860 |
| 75 | 38205 |
| 76 | 23475 |
| 77 | 11335 |
| 78 | 3670 |

TABLE 4

| Test compound | Cell growth inhibition rate (%) |
|---|---|
| 1 | 71.1 |
| 3 | 12.6 |
| 4 | 27.1 |
| 5 | 62.8 |
| 6 | 10.0 |
| 7 | 11.0 |
| 8 | 66.6 |
| 9 | 11.8 |
| 11 | 34.3 |
| 12 | 45.3 |
| 14 | 49.3 |
| 15 | 100.0 |
| 16 | 21.6 |
| 17 | 100.0 |
| 18 | 68.5 |
| 19 | 22.0 |
| 20 | 20.6 |
| 21 | 27.9 |
| 22 | 15.4 |
| 25 | 33.0 |
| 26 | 24.2 |
| 27 | 86.5 |
| 28 | 48.9 |
| 29 | 100.0 |
| 30 | 46.1 |
| 32 | 20.1 |
| 33 | 13.6 |
| 34 | 11.8 |
| 35 | 86.2 |
| 36 | 15.5 |
| 37 | 94.9 |
| 39 | 21.5 |
| 40 | 21.5 |
| 41 | 73.9 |
| 42 | 57.4 |
| 44 | 98.9 |
| 45 | 41.8 |
| 46 | 99.1 |
| 47 | 100.0 |
| 48 | 100.0 |
| 49 | 100.0 |
| 50 | 100.0 |
| 51 | 99.8 |
| 52 | 100.0 |
| 53 | 100.0 |
| 54 | 100.0 |
| 55 | 100.0 |
| 56 | 99.5 |
| 57 | 99.6 |
| 58 | 99.6 |
| 59 | 99.8 |
| 60 | 99.7 |
| 61 | 99.9 |
| 62 | 99.8 |
| 63 | 100.0 |
| 64 | 100.0 |
| 65 | 100.0 |
| 66 | 100.0 |
| 67 | 100.0 |
| 68 | 99.6 |
| 69 | 99.9 |
| 70 | 99.9 |
| 71 | 100.0 |
| 72 | 100.0 |
| 73 | 99.4 |
| 74 | 99.6 |
| 75 | 99.8 |
| 76 | 99.9 |
| 77 | 99.9 |
| 78 | 100.0 |

It is apparent from Tables 3 and 4 that suppression of tumor cell growth was invariably obtained in groups including the test compounds, indicating that the induction of differentiation to granulocytes and monocytemacrophage series was promoted by an increased expression of CD11b.

Pharmaceutical Test Example 3

Antiretrovirus efficacy test
(1) Cytotoxicity test (MTT Dye Uptake Assay)

Subcultured SC-1 (Feral mouse embryo) cells were washed with PBS$^{(-)}$ twice, exfoliated with 0.05% trypsin (Nissui Pharmaceutical) and pipetted into Eagle's MEM medium (E-MEM, Flow Laboratories)+5% fetal bovine serum (FBS). The cells were washed by centrifuging at 1200 rpm (25° C.) for 5 minutes (05PR-22, Hitachi Ltd.) and resuspended in the same medium. The viable cells were stained with 0.2% trypan blue (Wako Pure Chemical) and counted under the light microscope (BH-2, Olympus Optical Industry). The culture was then diluted with the medium to a concentration of $6 \times 10^4$ cells/ml.

A 96-well microplate (Corning) was filled with 0.1 ml/well of the test compound prepared in a concentration of 60 µg/ml and 0.1 ml aliquots of the SC-1 cell suspension ($6 \times 10^4$ cells/ml) prepared above were added to all the wells. This microplate was incubated in a 5% $CO_2$ incubator (Napco) at 37° C. for 3 days. After cultivation, $PBS^{(-)}$ (Nissui Pharmaceutical) containing 2.5 mg/ml of MTT (Dotite MTT, 3-(4,5-dimethyl-2-thiazolyl)-2,5-diphenyl-2H-tetrazolium, Wako Pure Chemical) was added in 0.01 ml aliquots to the wells and the plate was further incubated in the presence of 5% $CO_2$ at 37° C. for 3 hours. Thereafter, an eluent [10% SDS+0.01N HCl, Wako Pure Chemical] was added in 0.1 ml aliquots to the wells and the plate was further incubated in the presence of 5% $CO_2$ at 37° C. overnight. The optical density (O.D.) at 580 nm was determined using a Titertek Multiskan (MMC, Flow Laboratories).

From the optical density value found, the amount of dye taken up in viable cells was estimated and the cell growth inhibition rate (%) was calculated by means of the following equation.

Cell growth inhibition rate $(\%) = [1-(M/C)] \times 100$ wherein M represents the dye uptake in the test compound group and C represents the dye uptake in the control group.

(2) Viral growth inhibition test (UV-XC plaque reduction assay)

This test was performed according to the description of Viorogy 42, 1136–1139 (1970) in the following manner.

Subcultured SC-1 cells were washed with $PBS^{(-)}$ twice and exfoliated with 0.05% trypsin (Nissui Pharmaceutical) and pipetted into E-MEM medium (Flow Laboratories)+5% FBS. The cells were then washed by centrifuging at 1200 rpm (25° C.) for 5 minutes (05PR-22, Hitachi Ltd.) and resuspended in a similar medium. The viable cells were stained with 0.2% trypan blue (Wako Pure Chemical), counted under the light microscope (BH-2, Olympus Optical Co.) and diluted with the medium to a concentration of $1 \times 10^5$ cells/ml.

A 6-well plate (Costar) was filled with 1 ml aliquots of the above cell suspension, followed by addition of the medium in 1.5 ml aliquots to all the wells. This plate was incubated in a 5% $CO_2$ incubator (Napco) at 37° C.

After twenty four hours of incubation, the supernatant was discarded and LP-BM5 virus (murine leukemia virus) was added in 1 ml aliquots. Furthermore, 1.5 ml of the test compound was added to each well at a final concentration of 30 µg/ml. This plate was incubated in a 5% $CO_2$ incubator (Napco) at 37° C. for 3 days. After cultivation, the supernatant was discarded and the plate was irradiated with an ultraviolet lamp (15W×2) for 20 seconds. To the irradiated plate was added 2.5 ml of a suspension of $1 \times 10^5$ cells/ml of a subculture of XC (Rat sarcoma) cells and the plate was further incubated in a 5% $CO_2$ incubator at 37° C. for 3 days. After completion of cultivation, the wells were washed with $PBS^{(-)}$ once, fixed with methanol and stained with methylene blue diluted with methanol to 10 mg/ml. The plaques in each well were counted and the virus inhibition rate (%) was calculated by means of the following equation.

Virus inhibition rate $(\%) = [1-(M/C)] \times 100$ wherein M represents the number of plaques in the test compound group and C represents the number of plaques in the control group.

(3) Antiretrovirus effect

From the cell growth inhibition fate and virus inhibition rate determined in (1) and (2) above, the strength of virus growth inhibition was calculated by means of the following equation for use as an indicator of antiretrovirus activity. Strength of virus inhibition=virus growth inhibition rate/SC-1 cell growth inhibition rate The strength of virus inhibition thus determined is shown in Table 5.

TABLE 5

| Test compound | Strength of virus inhibition |
|---|---|
| 2 | 5.7 |
| 4 | 0.4 |
| 7 | 4.1 |
| 8 | 5.9 |
| 9 | 4.4 |
| 10 | 1.3 |
| 11 | 8.2 |
| 12 | 0.9 |
| 13 | 2.5 |
| 14 | 1.2 |
| 15 | 0.9 |
| 16 | 1.9 |
| 17 | 1.5 |
| 18 | 1.2 |
| 19 | 4.5 |
| 20 | 2.9 |
| 22 | 1.3 |
| 25 | 97.5 |
| 27 | 1.6 |
| 29 | 1.4 |
| 30 | 1.8 |
| 31 | 1.4 |
| 32 | 4.8 |
| 35 | 0.9 |
| 37 | 1.0 |
| 40 | 4.2 |
| 41 | 2.6 |
| 42 | 1.3 |

Pharmacological Test Example 4

(1) Cytokine release inhibition efficacy test 1

The effect on cytokines released on stimulation of peripheral blood from healthy man with lypopoly saccharide (LPS) was investigated in the following manner.

The test compound was dissolved in DMSO and diluted with RPMI-1640 medium to a predetermined concentration. As a control, DMSO alone was used as diluted in the same manner as above.

To RPMI-1640 medium (containing 100 U/ml of penicillin and 0.1 µg/ml of streptomycin) were added 10% peripheral blood from healthy man (heparin added), the test compound and LPS (E. coli 055:B5, 1 µg/ml), and the mixture was incubated in a 5% $CO_2$ incubator at 37° C. for 18–24 hours. The supernatant was recovered by centrifugation and used as a culture supernatant sample.

The various cytokines in the above sample were determined by enzyme-linked immunosorbent assay (ELISA) and the amount of each cytokine in the sample was estimated by comparison with the standard curve constructed with the corresponding cytokine.

The cytokines determined and the respective assay limits were as follows.

TNFα (Tumor necrosis factor α) . . . 20 pg/ml
IL-6 (Interleukin-6) . . . 20 pg/ml
IFNγ (Interferon-γ) . . . 20 pg/ml From the data generated at the final concentration of 30 µg/ml for each test compound, the release inhibition rate (%) with respect to the control was calculated. The values found are shown below in Table 6.

TABLE 6

| Test compound | TNF-α (% release inhibition) | IL-6 (% release inhibition) | IFN-γ (% release inhibition) |
|---|---|---|---|
| 1 | — | 38 | 19 |
| 2 | 12 | — | — |
| 3 | — | 48 | 21 |
| 4 | 44 | 33 | 7 |
| 7 | 1 | 34 | 9 |
| 8 | 83 | 54 | 94 |
| 9 | — | 42 | 48 |
| 10 | — | 43 | 9 |
| 11 | 95 | 67 | 98 |
| 12 | 92 | — | 97 |
| 13 | 54 | 31 | 83 |
| 14 | 75 | — | 91 |
| 15 | 54 | 57 | 84 |
| 16 | — | — | 20 |
| 17 | — | — | 89 |
| 18 | — | — | 66 |
| 19 | 32 | 45 | 27 |
| 20 | — | 28 | 14 |
| 22 | 26 | 15 | 83 |
| 24 | 42 | 23 | 59 |
| 25 | 80 | 43 | 65 |
| 27 | 91 | 61 | 97 |
| 29 | 62 | 68 | 28 |
| 30 | 79 | 57 | 97 |
| 31 | 74 | 39 | 87 |
| 32 | 91 | 2 | 90 |
| 33 | 9 | — | 27 |
| 35 | 14 | 38 | 90 |
| 36 | — | — | 78 |
| 37 | 20 | 55 | 77 |
| 39 | 97 | 90 | 93 |
| 40 | 44 | 12 | 83 |
| 41 | 95 | 18 | 98 |
| 42 | 31 | 6 | — |
| 43 | 20 | 28 | 13 |

In Table 6, the mark "–" means that no inhibition was recognized.

(2) Peripheral lymphocyte activation inhibitory activity test

This test was intended to evaluate the effect of each test compound on peripheral blood mononuclear cell (PBMC) by the MTT assay. The assay procedure was generally in accordance with the method developed by T. Mosmann [J. immunol. Methods. 65, 55–63 (1983)].

Thus, the peripheral blood from a healthy volunteer was subjected to density-gradient centrifugation using Ficoll-Paque (Pharmacia) to separate PBMC. The test compound was extemporaneously dissolved in 10 mg/ml of DMSO and diluted with 10% FCS-containing RPMI-1640 to a concentration of 120 µg/ml.

The test compound was extemporaneously dissolved in 10 mg/ml of DMSO and diluted with 10% FCS-containing RPMI-1640 to a concentration of 120 µg/ml. As a solvent, DMSO alone was used as diluted in the same manner as above.

In the above test, purified phytohemagglutinin:PHA, Welcome) was dissolved in 10% FCS-containing RPMI-1640 medium and sterilized by filtration for use.

In the presence of 30 µg/ml of the test compound (final concentration: 25 µl/well of the above-prepared solution) and 1 µg/ml (final concentration) of PHA, $10^5$ PBMC cells/100 µl/well were cultivated in 10% FCS-containing RPMI-1640 medium. After 3 days, a filtration-sterilized 2.5 mg/ml solution of MTT (Dojin) in PBS$^{(-)}$ was added in aliquots of 20 µl/well and the plate was incubated at 37° C. for 4 hours. Then, 10% SDS-0.01N HCl was added in aliquots of 100 µl/well for lysing the cells and the optical density in each well was determined at a wavelength of 580 nm. From the optical density value, the cell growth inhibition rate was calculated by means of the following equation. The test was performed in tetraplicates (n=4).

Cell growth inhibition rate (%) =

$$\left[ 1 - \left( \frac{\text{O.D. after addition of test compound} - \text{O.D. of test compound alone}}{\text{O.D. after addition of solvent} - \text{O.D. of solvent alone}} \right) \right] \times 100$$

The results are shown in Table 7.

TABLE 7

| Test compound | Cell growth inhibition rate (%) |
|---|---|
| 4 | 2.4 |
| 5 | 53.1 |
| 7 | 12.6 |
| 8 | 49.3 |
| 9 | 22.6 |
| 10 | 16.9 |
| 11 | 36.1 |
| 12 | 37.8 |
| 13 | 22.9 |
| 14 | 50.0 |
| 15 | 50.1 |
| 16 | 43.0 |
| 17 | 73.7 |
| 18 | 57.6 |
| 19 | 4.8 |
| 20 | 50.7 |
| 22 | 21.8 |
| 25 | 19.1 |
| 27 | 30.9 |
| 29 | 100.0 |
| 30 | 24.8 |
| 31 | 74.6 |
| 32 | 15.9 |
| 33 | 6.1 |
| 34 | 1.8 |
| 35 | 41.2 |
| 36 | 18.7 |
| 37 | 100.0 |
| 39 | 22.7 |
| 40 | 7.9 |
| 41 | 48.2 |
| 42 | 88.5 |

(3) Test for Activity of inhibiting shock death from endotoxin

The activity of inhibiting shock death from endotoxin was investigated by administering D-galactosamine and LPS to mice [Chris Galanos et al., Proc. Natl. Acad. Sci. USA. 76: 5939–5943 (1979)].

Test compounds were orally administered to BALB/c mice (male, 7-week old, purchased from SLC Co., Ltd.) in an amount of 50 mg/kg, or prednisolone was orally administered as a control to the mice in an amount of 5 mg/kg. One hour after administration, D-galactosamine (product of Wako Junyaku Co., Ltd.) was intraperitoneally administered to the mice in an amount of 20 mg/0.25 ml/body. Less than 1 minute thereafter, LPS (E. coli. 055:B5, product of Sigma) was intravenously administered to the mice in an amount of 10 µg/0.3 ml/body. On day 1, day 2 and day 3 after administration, the mice were observed to find out their life or death. The test compounds and prednisolone were suspended in a solvent (0.5% CMC, product of Daiichi Kogyo Seiyaku Co., Ltd.), while D-galactosamine and LPS were dissolved in saline. The mice were used in groups; each consisting of 10.

Table 8 shows the results.

TABLE 8

| Test compound | Survival ratio (%) | | |
|---|---|---|---|
| | day 1 | day 2 | day 3 |
| 2 | 40 | 40 | 40 |
| 8 | 40 | 40 | 30 |
| 15 | 70 | 70 | 70 |
| 23 | 80 | 70 | 70 |
| 27 | 40 | 40 | 40 |
| 29 | 50 | 50 | 50 |
| 35 | 40 | 40 | 40 |
| 37 | 60 | 50 | 50 |
| 41 | 50 | 50 | 50 |
| solvent | 10 | 10 | 10 |
| prednisolone | 100 | 100 | 100 |

Pharmacological Test Example 5

Anticancer efficacy test

Tumor cells (B16 mouse melanoma cells: $1 \times 10^4$ cells/mouse) were intradermally transplanted in the right abdominal region of mice (C57BL/6 mice, female, 6–9 weeks old, Charles River). On day 3 after transplantation, 5 or 50 mg/kg of the test compound was administered orally for 5 days and washed out by cessation of administration for 2 days. This procedure was repeated 4 times. The same test was also carried out in the vehicle control group (0.5% CMC, Diichi Kogyo). The tumor volume and body weight were determined daily and the results were compared with those in the vehicle control group. The test was carried out in groups of 8 animals.

The tumor volume was evaluated by measuring the major and minor diameters of the tumor with a slide gauge and calculating the volume of the tumor by means of the equation: tumor volume=(major diameter×minor diameter× minor diameter)/2. The anticancer activity of the test compound was evaluated in the percent inhibition of tumor volume relative to the vehicle group.

The results are shown in Table 9.

TABLE 9

| Test compound | Dosage (mg/kg) | Maximum inhibition rate (in days) | final inhibition rate (in days) |
|---|---|---|---|
| 2 | 5 | 76.9 (18) | 41.6 (30) |
| | 50 | 46.2 (14) | 22.5 (30) |
| 8 | 5 | 51.7 (25) | 50.0 (30) |
| | 50 | 59.2 (25) | 56.6 (30) |
| 15 | 5 | 62.1 (10) | 25.1 (30) |
| | 50 | 69.7 (14) | 44.0 (30) |
| 17 | 5 | 66.5 (30) | 66.5 (30) |
| | 50 | 61.6 (25) | 55.5 (30) |
| 23 | 5 | 54.0 (14) | 10.8 (30) |
| | 50 | 34.0 (22) | 2.3 (30) |
| 27 | 5 | 63.6 (10) | 39.0 (28) |
| | 50 | 83.9 (23) | 61.9 (28) |
| 29 | 5 | 80.8 (14) | 67.4 (28) |
| | 50 | 81.8 (10) | 61.7 (28) |
| 35 | 5 | 30.0 (23) | 25.5 (28) |
| | 50 | 4.2 (23) | −23.2 (28) |
| 37 | 5 | 58.5 (22) | 33.7 (30) |
| | 50 | 55.2 (14) | 33.3 (30) |
| 41 | 5 | 46.9 (30) | 46.9 (30) |
| | 50 | 62.6 (25) | 56.1 (30) |

In accordance with the present invention there is provided an apoptosis regulating agent. Based on its unique apoptosis regulating activity and cell differentiation inducing activity, this regulating agent can be effectively utilized as a chemotherapeutic agent for cancer. Moreover, based on its antiretrovirus activity, this agent can be effectively used as a therapeutic agent for the aforementioned various retrovirus-related diseases such as HIV- or HTLV-I-related diseases and C-type hepatitis. Furthermore, based on its cytokine production inhibitory effect, the agent is effective as a therapeutic agent for HIV- or HTLV-I-related diseases, infectious diseases, ARDS, CFS and various autoimmune diseases. It can also be used as an immunosuppression agent because of its lymphocyte activation inhibitory activity.

What is claimed is:

1. A method for treatment of leukemia and melanoma which method comprises administering to a host afflicted with such cancer an anti-cancer effective amount of at least one carbostyril derivative or a salt thereof selected from the group consisting of:

(1) a carbostyril derivative of the following general formula

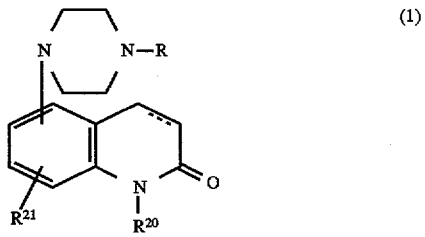

(1)

wherein R is a benzoyl group which may optionally have, on the phenyl ring thereof, one to three substituents each selected from the group consisting of a lower alkoxy group, a halogen atom, a lower alkyl group, a lower alkanoylamino group and a lower alkylthio group; a lower alkylenedioxy-benzoyl group; a hydrogen atom; a pyridylcarbonyl group; a lower alkanesulfonyl group; a lower alkynyl group; or a phenyl-lower alkyl group which may optionally have, on the phenyl ring thereof, one to three substituents each selected from the group consisting of a lower alkoxy group, a halogen atom and a lower alkyl group; the carbon-carbon bond between the 3 and 4 positions of the carbostyril skeleton is a single bond or a double bond; $R^{20}$ is a hydrogen atom, a lower alkyl group, a lower alkenyl group, a lower alkynyl group or a phenyl-lower alkyl group; and $R^{21}$ is a hydrogen atom or a lower alkoxy group; provided that when both $R^{20}$ and $R^{21}$ are hydrogen atoms, R is not a benzoyl group having a lower alkoxy group as a phenyl ring substituent; and a salt thereof;

(2) a carbostyril derivative of the following general formula

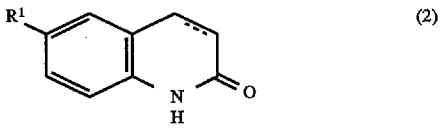

(2)

wherein $R^1$ is a group of the formula

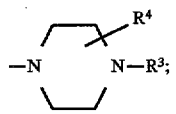

$R^3$ is a hydrogen atom or a benzoyl group; $R^4$ is an oxo group; and the carbon-carbon bond between the 3 and 4 positions of the carbostyril skeleton is a single bond or a double bond; and salts thereof;

(3) a carbostyril derivative of the following general formula

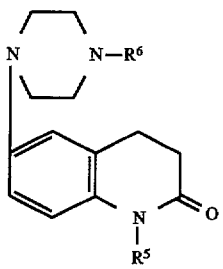

(3)

wherein $R^5$ is a lower alkanoyl group, a lower alkoxycarbonyl group, a lower alkoxycarbonyl-lower alkyl group, a phenyl-lower alkyl group having a lower alkanoyloxy group or a hydroxyl group on the phenyl ring thereof, or a benzoyl group which may optionally have, on the phenyl ring thereof, at least one substituent selected from the group consisting of a hydroxyl group and a amino group optionally having a lower alkyl group, or a naphthoyl group; and $R^6$ is a benzoyl group which may optionally have at least one lower alkoxy group on the phenyl ring thereof; and a salt thereof;

(4) a carbostyril derivative of the following general formula

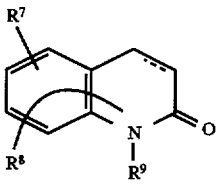

(4)

wherein $R^7$ is a piperazinyl group, $R^8$ is a hydrogen atom or a lower alkyl group; $R^9$ is a hydrogen atom or a phenyl-lower alkyl group; and the carbon-carbon bond between the 3 and 4 positions of the carbostyril skeleton is a single bond or a double bond; and a salt thereof;

(5) a carbostyril derivative of the following general formula

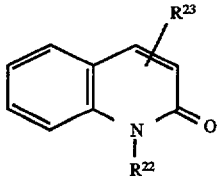

(5)

wherein $R^{22}$ is a $C_1$–$C_{16}$ alkyl group, a phenyl-lower alkoxycarbonyl-lower alkyl group, an amido-lower alkyl group which may optionally have at least one lower alkyl group, or a phenyl-lower alkyl group; and $R^{23}$ is a piperazinyl group which may optionally have a lower alkyl group in the 4 position of the piperazine ring; and a salt thereof;

(6) a carbostyril derivative of the following general formula

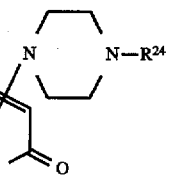

(6)

wherein $R^{24}$ is a hydrogen atom, a phenyl-lower alkyl group, a benzoyl-lower alkyl group, or a benzoyl group which may optionally have one to three of a lower alkoxy group or a lower alkylenedioxy group on the phenyl ring thereof; and a salt thereof; and (7) 6-[4-(3,4-dimethoxybenzoyl)-1-1,2,3,4-tetrahydropirazyl]-3,4-dihydrocarbostyril and a salt thereof.

2. The method according to claim 1, wherein the carbostyril derivative or salt thereof is the carbostyril derivative of the general formula (1) or a salt thereof.

3. The method according to claim 1, wherein the carbostyril derivative or salt thereof is the carbostyril derivative of the general formula (2) or a salt thereof.

4. The method according to claim 1, wherein the carbostyril derivative or salt thereof is the carbostyril derivative of the general formula (3) or a salt thereof.

5. The method according to claim 1, wherein the carbostyril derivative or salt thereof is the carbostyril derivative of the general formula (4) or a salt thereof.

6. The method according to claim 1, wherein the carbostyril derivative or salt thereof is the carbostyril derivative of the general formula (5) or a salt thereof.

7. The method according to claim 1, wherein the carbostyril derivative or salt thereof is the carbostyril derivative of the general formula (6) or a salt thereof.

8. The method according to claim 1, wherein the carbostyril derivative or salt thereof is 6-[4-(3,4-Dimethoxybenzoyl)-1-1,2,3,4-tetrahydropirazyl]-3,4-dihydrocarbostyril or a salt thereof.

9. A method for treatment of cancer which is sensitive to said treatment which method comprises administering to a host afflicted with such cancer an anti-cancer effective amount of at least one carbostyril derivative or a salt thereof selected from the group consisting of:

(1) a carbostyril derivative of the following general formula

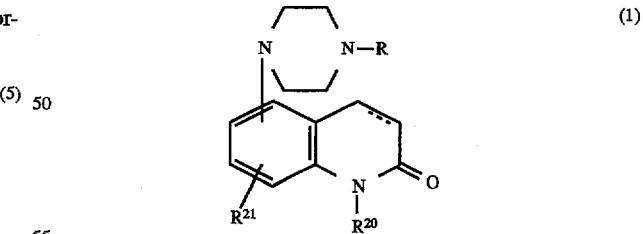

(1)

wherein R is a benzoyl group which may optionally have, on the phenyl ring thereof, one to three substituents each selected from the group consisting of a lower alkoxy group, a halogen atom, a lower alkyl group, a lower alkanoylamino group and a lower alkylthio group; a lower alkylenedioxybenzoyl group; a hydrogen atom; a pyridylcarbonyl group; a lower alkanesulfonyl group; a lower alkynyl group; or a phenyl-lower alkyl group which may optionally have, on the phenyl ring thereof, one to three substituents each selected from the group consisting of a lower alkoxy group, a halogen atom and a lower alkyl group; the carbon-carbon bond between the 3 and 4 positions of the carbostyril skeleton is a single bond or a double bond; $R^{20}$ is a hydrogen atom, a lower alkyl group, a lower alkenyl group, a lower alkynyl group or a phenyl-lower alkyl group; and $R^{21}$ is a hydrogen atom or a lower alkoxy group; provided that when both $R^{20}$ and $R^{21}$ are hydrogen atoms, R is not a benzoyl group having a lower alkoxy group as a phenyl ring substituent; and a salt thereof;

(2) a carbostyril derivative of the following general formula

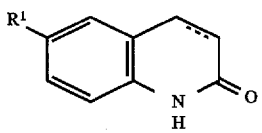
(2)

wherein $R^1$ is a group of the formula

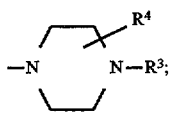

$R^3$ is a hydrogen atom or a benzoyl group; $R^4$ is an oxo group; and the carbon-carbon bond between the 3 and 4 positions of the carbostyril skeleton is a single bond or a double bond; and salts thereof;

(3) a carbostyril derivative of the following general formula

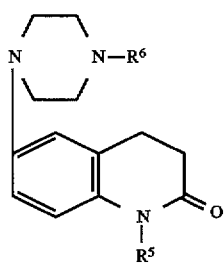
(3)

wherein $R^5$ is a lower alkanoyl group, a lower alkoxycarbonyl group, a lower alkoxycarbonyl-lower alkyl group, a phenyl-lower alkyl group having a lower alkanoyloxy group or a hydroxyl group on the phenyl ring thereof, or a benzoyl group which may optionally have, on the phenyl ring thereof, at least one substituent selected from the group consisting of a hydroxyl group and a amino group optionally having a lower alkyl group, or a naphthoyl group; and $R^6$ is a benzoyl group which may optionally have at least one lower alkoxy group on the phenyl ring thereof; and a salt thereof;

(4) a carbostyril derivative of the following general formula

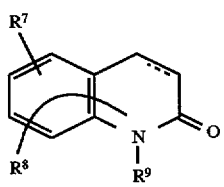
(4)

wherein $R^7$ is a piperazinyl group, $R^8$ is a hydrogen atom or a lower alkyl group; $R^5$ is a hydrogen atom or a phenyl-lower alkyl group; and the carbon-carbon bond between the 3 and 4 positions of the carbostyril skeleton is a single bond or a double bond; and a salt thereof;

(5) a carbostyril derivative of the following general formula

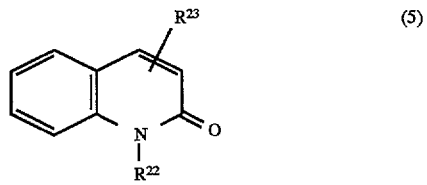
(5)

wherein $R^{22}$ is a $C_{1-16}$ alkyl group, a phenyl-lower alkoxycarbonyl-lower alkyl group, an amido-lower alkyl group which may optionally have at least one lower alkyl group, or a phenyl-lower alkyl group; and $R^{23}$ is a piperazinyl group which may optionally have a lower alkyl group in the 4 position of the piperazine ring; and a salt thereof;

(6) a carbostyril derivative of the following general formula

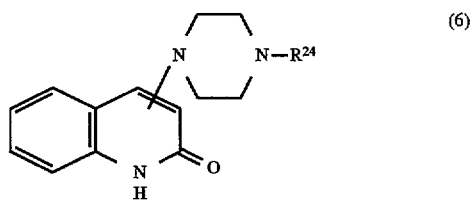
(6)

wherein $R^{24}$ is a hydrogen atom, a phenyl-lower alkyl group, a benzoyl-lower alkyl group, or a benzoyl group which may optionally have one to three of a lower alkoxy group or a lower alkylenedioxy group on the phenyl ring thereof; and a salt thereof; and (7) 6-[4-(3,4-dimethoxybenzoyl)-1-1,2,3,4-tetrahydropirazyl]-3,4-dihydrocarbostyril and a salt thereof.

10. The method according to claim 9, wherein the carbostyril derivative is according to formula (1) or salt thereof.

11. The method according to claim 9, wherein the carbostyril derivative is according to formula (2) or salt thereof.

12. The method according to claim 9, wherein the carbostyril derivative is according to formula (3) or salt thereof.

13. The method according to claim 9, wherein the carbostyril derivative is according to formula (4) or salt thereof.

14. The method according to claim 9, wherein the carbostyril derivative is according to formula (5) or salt thereof.

15. The method according to claim 9, wherein the carbostyril derivative is according to formula (6) or salt thereof.

16. The method according to claim 9, wherein the carbostyril derivative is 6-[4-(3,4-dimethoxybenzoyl)-1-1,2,3,4-tetrahydropirazyl]-3,4-dihydrocarbostyril and a salt thereof.

* * * * *

UNITED STATES PATENT AND TRADEMARK OFFICE
CERTIFICATE OF CORRECTION

PATENT NO. : 5,691,341
DATED : November 25, 1997
INVENTOR(S) : Nakai et al

It is certified that error appears in the above-identified patent and that said Letters Patent is hereby corrected as shown below:

On title page,

Item [30], delete "5-220373" and insert therefor -- 4-220373--.

Signed and Sealed this

Twenty-fourth Day of March, 1998

Attest:

BRUCE LEHMAN

*Attesting Officer*  *Commissioner of Patents and Trademarks*